US010980544B2

(12) United States Patent
Bowman

(10) Patent No.: US 10,980,544 B2
(45) Date of Patent: Apr. 20, 2021

(54) IMPLANT DELIVERY SYSTEM

(71) Applicant: MicroVention, Inc., Aliso Viejo, CA (US)

(72) Inventor: Heath Bowman, Trabuco Canyon, CA (US)

(73) Assignee: MicroVention, Inc., Aliso Viejo, CA (US)

(*) Notice: Subject to any disclaimer, the term of this patent is extended or adjusted under 35 U.S.C. 154(b) by 383 days.

(21) Appl. No.: 15/839,671

(22) Filed: Dec. 12, 2017

(65) Prior Publication Data

US 2018/0110528 A1 Apr. 26, 2018

Related U.S. Application Data

(63) Continuation of application No. 14/685,312, filed on Apr. 13, 2015, now Pat. No. 9,867,622.

(60) Provisional application No. 61/978,686, filed on Apr. 11, 2014.

(51) Int. Cl.
*A61F 2/95* (2013.01)
*A61B 17/12* (2006.01)
*A61F 2/82* (2013.01)
*A61B 17/00* (2006.01)
*A61B 90/00* (2016.01)

(52) U.S. Cl.
CPC .. *A61B 17/12109* (2013.01); *A61B 17/12154* (2013.01); *A61B 2017/0003* (2013.01); *A61B 2017/00929* (2013.01); *A61B 2017/12068* (2013.01); *A61B 2090/0808* (2016.02); *A61F 2/82* (2013.01)

(58) Field of Classification Search
CPC ... A61F 2/82; A61F 2/95; A61F 2/958; A61B 17/12; A61B 17/12109; A61B 17/12154; A61B 2017/12068; A61B 2017/1205
See application file for complete search history.

(56) References Cited

U.S. PATENT DOCUMENTS

| 3,324,280 | A | | 6/1967 | Cheney et al. | |
| 4,346,712 | A | | 8/1982 | Handa et al. | |
| 4,885,217 | A | * | 12/1989 | Hoge | H01M 4/96 429/407 |
| 5,108,407 | A | | 4/1992 | Geremia et al. | |
| 5,122,136 | A | | 6/1992 | Guglielmi et al. | |
| 5,217,484 | A | | 6/1993 | Marks | |
| 5,354,295 | A | | 10/1994 | Guglielmi et al. | |

(Continued)

FOREIGN PATENT DOCUMENTS

| EP | 0707830 A1 | 4/1996 |
| EP | 0750886 A1 | 1/1997 |

(Continued)

OTHER PUBLICATIONS

WIPO, U.S. International Search Authority, International Search Report and Written Opinion dated Jul. 9, 2015 in International Patent Application No. PCT/US2015/025594, 10 pages.

*Primary Examiner* — Vi X Nguyen
(74) *Attorney, Agent, or Firm* — Inskeep IP Group, Inc.

(57) ABSTRACT

A system and method of delivering and detaching an implant within a body of a patient is described. A tether connects an implant with a delivery device. The delivery device includes a heater through which the tether passes. The inner lumen of the delivery system pusher may accommodate the lead wires which connect to the heater.

17 Claims, 24 Drawing Sheets

(56) References Cited

U.S. PATENT DOCUMENTS

| | | |
|---|---|---|
| 5,382,259 A | 1/1995 | Phelps et al. |
| 5,470,338 A | 11/1995 | Whitfield et al. |
| 5,540,680 A | 7/1996 | Guglielmi et al. |
| 5,582,619 A | 12/1996 | Ken |
| 5,759,161 A | 6/1998 | Ogawa et al. |
| 5,846,210 A | 12/1998 | Ogawa et al. |
| 5,853,418 A | 12/1998 | Ken et al. |
| 5,855,578 A | 1/1999 | Guglielmi et al. |
| 5,873,835 A | 2/1999 | Hastings et al. |
| 5,895,385 A | 4/1999 | Guglielmi et al. |
| 5,925,037 A | 7/1999 | Guglielmi et al. |
| 5,928,226 A | 7/1999 | Guglielmi et al. |
| 5,941,888 A | 8/1999 | Wallace et al. |
| 5,944,714 A | 8/1999 | Guglielmi et al. |
| 5,944,733 A | 8/1999 | Engelson |
| 5,947,962 A | 9/1999 | Guglielmi et al. |
| 5,976,126 A | 11/1999 | Guglielmi et al. |
| 5,976,131 A | 11/1999 | Guglielmi et al. |
| 6,010,498 A | 1/2000 | Guglielmi |
| 6,066,133 A | 5/2000 | Guglielmi et al. |
| 6,083,220 A | 7/2000 | Guglielmi et al. |
| 6,158,206 A | 12/2000 | Ogawa |
| 6,238,415 B1 | 5/2001 | Sepetka et al. |
| 6,277,126 B1 | 8/2001 | Barrey et al. |
| 6,478,773 B1 | 11/2002 | Gandhi et al. |
| 6,500,149 B2 | 12/2002 | Gandhi et al. |
| 6,602,269 B2 | 8/2003 | Wallace et al. |
| 6,645,240 B2 | 11/2003 | Yee |
| 6,743,251 B1 | 6/2004 | Eder |
| 6,807,446 B2 | 10/2004 | Fenn et al. |
| 6,849,081 B2 | 2/2005 | Sepetka et al. |
| 6,966,892 B2 | 11/2005 | Gandhi et al. |
| 7,048,719 B1 | 5/2006 | Monetti |
| 7,166,122 B2 | 1/2007 | Aganon et al. |
| RE41,029 E | 12/2009 | Guglielmi et al. |
| RE42,662 E | 8/2011 | Guglielmi et al. |
| RE42,756 E | 9/2011 | Guglielmi et al. |
| 8,182,506 B2 | 5/2012 | Fitz et al. |
| 2001/0029352 A1 | 10/2001 | Gandhi et al. |
| 2001/0041898 A1 | 11/2001 | Barry et al. |
| 2002/0029035 A1 | 3/2002 | Lee et al. |
| 2002/0091380 A1 | 7/2002 | Wheelock et al. |
| 2002/0099408 A1 | 7/2002 | Marks et al. |
| 2002/0123755 A1 | 9/2002 | Lowe et al. |
| 2002/0188341 A1 | 12/2002 | Elliott |
| 2004/0034363 A1 | 2/2004 | Wilson et al. |
| 2004/0220563 A1 | 11/2004 | Eder |
| 2006/0116708 A1 | 6/2006 | Ogawa et al. |
| 2006/0173488 A1 | 8/2006 | Takeuchi et al. |
| 2006/0241682 A1 | 10/2006 | Kurz |
| 2006/0271098 A1 | 11/2006 | Peacock, III |
| 2007/0239196 A1 | 11/2007 | Pomeranz |
| 2008/0228215 A1 | 9/2008 | Strauss et al. |
| 2008/0306503 A1 | 12/2008 | Que et al. |
| 2009/0062726 A1 | 3/2009 | Ford et al. |
| 2009/0270901 A1 | 10/2009 | Kelleher et al. |
| 2010/0160944 A1* | 6/2010 | Teoh ............... A61B 17/12022 606/191 |
| 2010/0160983 A1* | 6/2010 | Runco .................. A61F 2/4611 606/86 A |
| 2010/0268204 A1 | 10/2010 | Tieu et al. |
| 2010/0268252 A1 | 10/2010 | Chen et al. |
| 2012/0116350 A1 | 5/2012 | Strauss et al. |
| 2013/0085520 A1 | 4/2013 | Liang et al. |
| 2013/0261656 A1 | 10/2013 | Lorenzo |
| 2013/0261657 A1 | 10/2013 | Lorenzo |
| 2014/0058434 A1 | 2/2014 | Jones et al. |
| 2014/0142611 A1 | 5/2014 | Plaza et al. |

FOREIGN PATENT DOCUMENTS

| | | |
|---|---|---|
| EP | 0803230 A2 | 10/1997 |
| EP | 0914803 A1 | 5/1999 |
| EP | 1005837 A2 | 6/2000 |
| EP | 1329196 A1 | 7/2003 |
| EP | 1366720 A1 | 12/2003 |
| WO | WO1993/016650 A1 | 9/1993 |
| WO | WO 2004/010877 A1 | 2/2004 |

* cited by examiner

Direct Current (DC)
Signaling

Alternating Current (AC)
Signaling

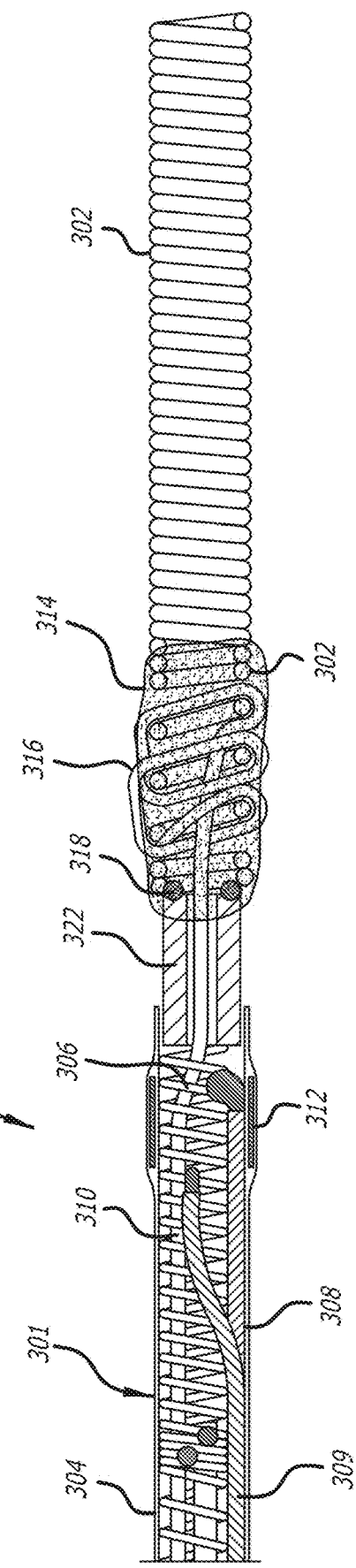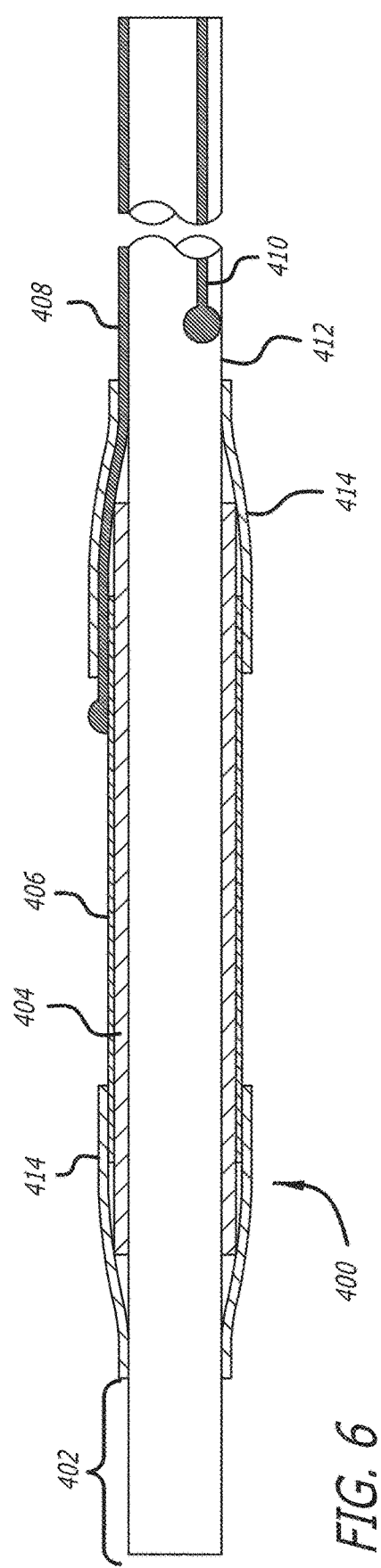

IMPLANT DELIVERY SYSTEM

RELATED APPLICATIONS

This application is a continuation of and claims priority to U.S. patent application Ser. No. 14/685,312 filed Apr. 13, 2015 entitled Implant Delivery System, which is the nonprovisional of and claims priority to U.S. Provisional Application Ser. No. 61/978,686 filed Apr. 11, 2014 entitled Implant Delivery System, both which are hereby incorporated herein by reference in their entireties.

FIELD OF THE INVENTION

The present invention relates to systems and methods for delivering implant devices to a target site or location within the body of a patient. The present invention also relates to a method of detecting implant detachment within the body of a patient.

BACKGROUND OF THE INVENTION

Delivery of implantable therapeutic devices by less invasive means has been demonstrated to be desirable in numerous clinical situations. For example, vascular embolization has been used to control vascular bleeding, to occlude the blood supply to tumors, to occlude fallopian tubes, and to occlude vascular aneurysms, particularly intracranial aneurysms. In recent years, vascular embolization for the treatment of aneurysms has received much attention. Implants used to treat aneurysms are often convoluted or coiled lengths of wound wire and are referred to as "microcoils." Microcoils work by filling an aneurysm causing the blood flow through the aneurysm to slow or stop, thereby inducing thrombosis within the aneurysm.

Microcoils are extremely flexible and have very little structural integrity. In order to make them easier to retrieve and reposition, recent efforts have been directed to making them stretch-resistant. For example, a stretch-resistant embolic coil having a stretch-resistant member passing through the interior lumen of the coil is described in U.S. Pat. No. 5,582,619 to Ken. US Patent Publication No. 2004/0034363 to Wilson also discloses an embolic coil with a stretch resistant member having a distal end attached near the distal end of the coil and a proximal end of the member attached to a delivery catheter.

Several different treatment modalities have been employed in the prior art for deploying implant devices. For example, numerous repositionable detachment systems for implant devices have been described in the prior art including U.S. Pat. No. 5,895,385 to Guglielmi et al. and U.S. Pat. No. 5,108,407 to Geremia et al., the contents of which are hereby incorporated by reference. Several systems, such as those disclosed in U.S. Pat. No. 6,500,149 to Gandhi et al. and U.S. Pat. No. 4,346,712 to Handa et al., the contents of which are hereby incorporated by reference, describe the use of a heater to detach and deploy the implant device.

While implant delivery and detachment systems are known in the art, they do not provide the user feedback that the implant has indeed detached from the delivery device. This is especially important in cases where the detachment relies on the application of heat or an electrolytic process where an element of time is involved. These delivery devices leave the user in the position of wondering whether heat etc., has been applied long enough to cause detachment.

Hence, there exists a need for a method of detecting whether an implant has properly and effectively detached within the body of a patient.

SUMMARY OF THE INVENTION

The present invention is an implant delivery and detachment system used to position and deploy implantable devices such as coils, stents, filters, and the like within a body cavity including, but not limited to, blood vessels, fallopian tubes, malformations such as fistula and aneurysms, heart defects (e.g. left atrial appendages and sepal openings), and other luminal organs.

The system comprises an implant, a delivery catheter (generically referred to as the pusher or delivery pusher), a detachable joint for coupling the implant to the pusher, a heat generating apparatus (generically referred to as the heater), and a power source to apply energy to the heater.

The present invention also includes a method for detecting detachment of an implant. In particular, detachment of an implant is detected by measuring the change in the electrical resistance of the delivery system.

The present invention may also be used in conjunction with the delivery mechanism disclosed in U.S. patent application Ser. No. 11/212,830 filed Aug. 25, 2005 entitled "Thermal detachment system for implanting devices," which is incorporated by reference herein in its entirety.

In one aspect of the present invention, the implant is coupled to the pusher using a tether, string, thread, wire, filament, fiber, or the like. Generically this is referred to as the tether. The tether may be in the form of a monofilament, rod, ribbon, hollow tube, or the like. Many materials can be used to detachably join the implant to the pusher. One class of materials is polymers such as polyolefin, polyolefin elastomer such as those made by Dow marketed under the trade name Engage or Exxon marketed under the trade name Affinity, polyethylene, polyester (PET), polyamide (Nylon), polyurethane, polypropylene, block copolymer such as PEBAX or Hytrel, and ethylene vinyl alcohol (EVA); or rubbery materials such as silicone, latex, and Kraton. In some cases, the polymer may also be cross-linked with radiation to manipulate its tensile strength and melt temperature. Another class of materials is metals such as nickel titanium alloy (Nitinol), gold, and steel. The selection of the material depends on the capacity of the material to store potential energy, the melting or softening temperature, the power used for detachment, and the body treatment site. The tether may be joined to the implant and/or the pusher by welding, knot tying, soldering, adhesive bonding, or other means known in the art. In one embodiment where the implant is a coil, the tether may run through the inside lumen of the coil and be attached to the distal end of the coil. This design not only joins the implant to the pusher, but also imparts stretch resistance to the coil without the use of a secondary stretch resistant member. In other embodiments where the implant is a coil, stent, or filter; the tether is attached to the proximal end of the implant.

In another aspect of the present invention, the tether detachably coupling the implant to the pusher acts as a reservoir of stored (i.e. potential) energy that is released during detachment. This advantageously lowers the time and energy required to detach the implant because it allows the tether to be severed by application of heat without necessarily fully melting the material. The stored energy also may exert a force on the implant that pushes it away from the delivery catheter. This separation tends to make the system more reliable because it may prevent the tether from resolidifying and holding the implant after detachment. Stored energy may be imparted in several ways. In one embodiment, a spring is disposed between the implant and pusher. The spring is compressed when the implant is attached to the pusher by joining one end of the tether to one of either the pusher or implant, pulling the free end of the tether until the spring is at least partially compressed, then affixing the free end of the tether to the other of the implant or the pusher. Since both ends of the tether are restrained, potential energy in the form of tension on the tether (or compression in the spring) is stored within the system. In another embodiment, one end of the tether is fixed as in the previous embodiment, and then the tether is placed in tension by pulling on the free end of the tether with a pre-determined force or displacement. When the free end of the tether is then affixed, the elongation (i.e. elastic deformation) of the tether material itself stores energy.

In another aspect of the present invention, a heater is disposed on or within the pusher, typically, but not necessarily, near the distal end of the pusher. The heater may be attached to the pusher by, for example, soldering, welding, adhesive bonding, mechanical boding, or other techniques known in the art. The heater may be in the form of a wound coil, heat pipe, hollow tube, band, hypotube, solid bar, toroid, or similar shape. The heater may be made from a variety of materials such as steel, chromium cobalt alloy, platinum, silver, gold, tantalum, tungsten, mangalin, chromium nickel alloy available from California Fine Wire Company under the trade name Stable Ohm, conductive polymer, or the like. The tether is disposed in proximity to the heater. The tether may pass through the lumen of a hollow or coil-type heater or may be wrapped around the heater. Although the tether may be disposed in direct contact with the heater, this is not necessary. For ease of assembly, the tether may be disposed be in proximity to, but not actually touching, the heater.

The delivery catheter or pusher is an elongate member with distal and proximal ends adapted to allow the implant to be maneuvered to the treatment site. The pusher comprises a core mandrel and one or more electrical leads to supply power to the heater. The pusher may taper in dimension and/or stiffness along the length, with the distal end usually being more flexible than the proximal end. In one embodiment, the pusher is adapted to be telescopically disposed within a delivery conduit such as a guide catheter or microcatheter. In another embodiment, the pusher contains an inner lumen allowing it to be maneuvered over a guide wire. In still another embodiment, the pusher can be maneuvered directly to the treatment site without a secondary device. The pusher may have a radiopaque marking system visible with fluoroscopy that allows it to be used in conjunction with radiopaque markings on the microcatheter or other adjunctive devices.

In another aspect of the present invention, the core mandrel is in the form of a solid or hollow shaft, wire, tube, hypotube, coil, ribbon, or combination thereof. The core mandrel may be made from plastic materials such as PEEK, acrylic, polyamide, polyimide, Teflon, acrylic, polyester, block copolymer such as PEBAX, or the like. The plastic member(s) may be selectively stiffened along the length with reinforcing fibers or wires made from metal, glass, carbon fiber, braid, coils, or the like. Alternatively, or in combination with plastic components, metallic materials such as stainless steel, tungsten, chromium cobalt alloy, silver, copper, gold, platinum, titanium, nickel titanium alloy (Nitinol), and the like may be used to form the core mandrel. Alternatively, or in combination with plastic and/or metallic components, ceramic components such as glass, optical fiber, zirconium, or the like may be used to form the core mandrel. The core mandrel may also be a composite of materials. In one embodiment, the core mandrel comprises an inner core of radiopaque material such as platinum or tantalum and an outer covering of kink-resistant material such as steel or chromium cobalt. By selectively varying the thickness of the inner core, radiopaque identifiers can be provided on the pusher without using secondary markers. In another embodiment, a core material, for example stainless steel, with desirable material properties such as kink resistance and/or compressive strength is selectively covered (by, for example, plating, drawing, or similar methods known in the art) with a low electrical resistance material such as copper, aluminum, gold, or silver to enhance its electrical conductivity, thus allowing the core mandrel to be used as an electrical conductor. In another embodiment, a core material, for example, glass or optical fiber, with desirable properties such as compatibility with Magnetic Resonance Imaging (MRI), is covered with a plastic material such as PEBAX or polyimide to prevent the glass from fracturing or kinking.

In another aspect of the present invention, the heater is attached to the pusher, and then one or more electrical conductors are attached to the heater. In one embodiment a pair of conductive wires run substantially the length of the pusher and are coupled to the heater near the distal end of the pusher and to electrical connectors near the proximal end of the pusher. In another embodiment, one conductive wire runs the substantially the length of the pusher and the core mandrel itself is made from a conductive material or coated with a conductive material to act as a second electrical lead. The wire and the mandrel are coupled to the heater near the distal end and to one or more connectors near the proximal end of the pusher. In another embodiment, a bipolar conductor is coupled to the heater and is used in conjunction with radiofrequency (RF) energy to power the heater. In any of the embodiments, the conductor(s) may run in parallel to the core mandrel or may pass through the inner lumen of a substantially hollow core mandrel (for example, a hypotube).

In another aspect of the present invention, an electrical and/or thermally insulating cover or sleeve may be placed over the heater. The sleeve may be made from insulating materials such as polyester (PET), Teflon, block copolymer, silicone, polyimide, polyamide, and the like.

In another aspect of the present invention, electrical connector(s) are disposed near the proximal end of the pusher so that the heater can be electrically connected to a power source through the conductors. In one embodiment, the connectors are in the form of a plug with one or more male or female pins. In another embodiment, the connector(s) are tubes, pins, or foil that can be connected with clip-type connectors. In another embodiment, the connector(s) are tubes, pins, or foil that are adapted to mate with an external power supply.

In another aspect of the present invention, the pusher connects to an external power source so that the heater is electrically coupled to the power source. The power source may be from battery(s) or connected to the electrical grid by a wall outlet. The power source supplies current in the form of direct current (DC), alternating current (AC), modulated direct current, or radiofrequency (RF) at either high or low frequency. The power source may be a control box that operates outside of the sterile field or may be a hand-held device adapted to operate within a sterile field. The power source may be disposable, rechargeable, or may be reusable with disposable or rechargeable battery(s).

In another aspect of the present invention, the power source may comprise an electronic circuit that assists the user with detachment. In one embodiment, the circuit detects detachment of the implant and provides a signal to the user when detachment has occurred. In another embodiment, the circuit comprises a timer that provides a signal to the user when a pre-set length of time has elapsed. In another embodiment, the circuit monitors the number of detachments and provides a signal or performs an operation such as locking the system off when a pre-set number of detachments have been performed. In another embodiment, the circuit comprises a feedback loop that monitors the number of attachment attempts and increases the current, voltage, and/or detachment time in order to increase the likelihood of a successful detachment.

In another aspect of the present invention, the construction of the system allows for extremely short detachment time. In one embodiment the detachment time is less than 1 second.

In another aspect of the present invention, the construction of the system minimizes the surface temperature of the device during detachment. In one embodiment, the surface temperature at the heater during detachment is under 50° C. In another embodiment, the surface temperature at the heater during detachment is under 42° C.

In another aspect of the present invention, detachment of the implant is detected by measuring a change in the electrical resistance of the delivery system, specifically the heater zone, to detect implant detachment.

In another aspect of the present invention, a delivery system utilizing a pusher is described wherein said pusher accommodates lead wires which connect to a heater.

In another aspect of the present invention, a hypotube heater is described.

In another aspect of the present invention, a hypotube heater with staggered sections is described.

In another aspect of the present invention, an implant delivery system utilizing a hypotube heater described.

In another aspect of the present invention, a heater with an enlarged distal section is described.

In another aspect of the present invention, an implant delivery system utilizing an enlarged distal section is described.

In another aspect of the present invention, an implant delivery system utilizing multiple hypotube heaters is described.

These and other aspects and features of the present invention will be appreciated upon consideration of the following drawings and detailed descriptions.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which:

FIG. 4 illustrates a cross-sectional side view of a third embodiment of a detachment system according to the present invention;

FIG. 6 illustrates a cross-sectional side view of an electrical connector of a detachment system according to the present invention;

FIGS. 19-26A illustrate various parts of an implant delivery system according to another embodiment.

FIGS. 30-31C illustrate a staggered hypotube heater utilized in an implant delivery system.

DETAILED DESCRIPTION OF THE INVENTION

Figure 1:
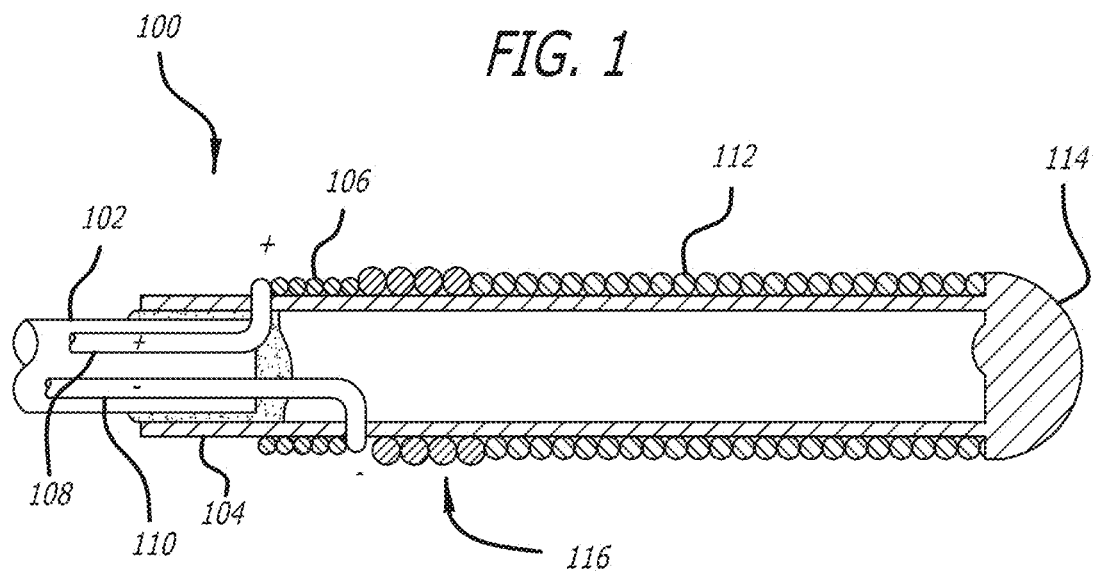
FIG. 1 illustrates a cross-sectional side view of a first embodiment of a detachment system according to the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

U.S. Pat. No. 8,182,506, US20100268204, US20110301686 are hereby incorporated by reference in their entirety.

Turning to FIG. 1, a detachment system 100 of the present invention, and specifically the distal portion of the detachment system 100, is illustrated. The detachment system 100 includes a pusher 102 that is preferably flexible. The pusher 102 is configured for use in advancing an implant device 112 into and within the body of a patient and, specifically, into a target cavity site for implantation and delivery of the implant device 112. Potential target cavity sites include but are not limited to blood vessels and vascular sites (e.g., aneurysms and fistula), heart openings and defects (e.g., the left atrial appendage), and other luminal organs (e.g., fallopian tubes).

A stretch-resistant tether 104 detachably couples the implant 112 to the pusher 102. In this example, the tether 104 is a plastic tube that is bonded to the pusher 102. A substantially solid cylinder could also be a design choice for the tether 104. The stretch resistant tether 104 extends at least partially through the interior lumen of an implant device 112.

Near the distal end of the pusher 102, a heater 106 is disposed in proximity to the stretch resistant tether 104. The heater 106 may be wrapped around the stretch resistant tether 104 such that the heater 106 is exposed to or otherwise in direct contact with the blood or the environment, or alternatively may be insulated by a sleeve, jacket, epoxy, adhesive, or the like. The pusher 102 comprises a pair of electrical wires, positive electrical wire 108 and negative electrical wire 110. The wires 108 and 110 are coupled to the heater 106 by any suitable means, such as, e.g., by welding or soldering.

The electrical wires 108, 110 are capable of being coupled to a source of electrical power (not shown). As illustrated the negative electrical wire 110 is coupled to the distal end of the heater 106 and the positive electrical wire 108 is coupled to the proximal end of the heater 106. In another embodiment, this configuration may be reversed, i.e., the negative electrical wire 110 is coupled to the proximal end of the heater 106 while the positive electrical wire 108 is coupled to the distal end of the heater 106.

Energy is applied to the heater 106 from the electrical wires 108, 110 in order to sever the portion of the tether 104 in the proximity of the heater 106. It is not necessary for the heater 106 to be in direct contact with the tether 104. The heater 106 merely should be in sufficient proximity to the tether 104 so that heat generated by the heater 106 causes the tether 104 to sever. As a result of activating the heater 106, the section of the stretch resistant tether 104 that is approximately distal from the heater 106 and within the lumen of an implant device 112 is released from the pusher 102 along with the implant device 112.

As illustrated, the implant device 112 is an embolic coil. An embolic coil suitable for use as the implant device 112 may comprise a suitable length of wire formed into a helical microcoil. The coil may be formed from a biocompatible material including platinum, rhodium, palladium, rhenium, tungsten, gold, silver, tantalum, and various alloys of these metals, as well as various surgical grade stainless steels. Specific materials include the platinum/tungsten alloy known as Platinum 479 (92% Pt, 8% W, available from Sigmund Cohn, of Mount Vernon, N.Y.) and nickel/titanium alloys (such as the nickel/titanium alloy known as Nitinol).

Another material that may be advantageous for forming the coil is a bimetallic wire comprising a highly elastic metal with a highly radiopaque metal. Such a bimetallic wire would also be resistant to permanent deformation. An example of such a bimetallic wire is a product comprising a Nitinol outer layer and an inner core of pure reference grade platinum, available from Sigmund Cohn, of Mount Vernon, N.Y., and Anomet Products, of Shrewsbury, Mass.

Commonly-assigned U.S. Pat. No. 6,605,101 provides a further description of embolic coils suitable for use as the implant device 112, including coils with primary and secondary configurations wherein the secondary configuration minimizes the degree of undesired compaction of the coil after deployment. The disclosure of U.S. Pat. No. 6,605,101 is fully incorporated herein by reference. Furthermore, the implant device 112 may optionally be coated or covered with a hydrogel or a bioactive coating known in the art.

The coil-type implant device 112 resists unwinding because the stretch resistant tether 104 that extends through the lumen of the implant device 112 requires substantially more force to plastically deform than the implant device 112 itself. The stretch resistant tether 104 therefore assists in preventing the implant device 112 from unwinding in situations in which the implant device 112 would otherwise unwind.

During assembly, potential energy may be stored within the device to facilitate detachment. In one embodiment, an optional spring 116 is placed between the heater 106 and the implant device 112. The spring is compressed during assembly and the distal end of the tether 104 may be tied or coupled to the distal end of the implant device 112, or may be melted or otherwise formed into an atraumatic distal end 114.

In one embodiment, the stretch resistant tether 104 is made from a material such as a polyolefin elastomer, polyethylene, or polypropylene. One end of the tether 104 is attached to the pusher 102 and the free end of the tether 104 is pulled through the implant 112 with the proximal end of the implant 112 flush to either the heater 106 (if no spring 116 is present) or to the compressed spring 116. A pre-set force or displacement is used to pre-tension the tether 104, thus storing energy in an axial orientation (i.e. co-linear or parallel to the long axis of the pusher 102) within the tether 104. The force or displacement depends on the tether material properties, the length of the tether 104 (which itself depends on the tether's attachment point on the pusher and the length of the implant). Generally, the force is below the elastic limit of the tether material, but sufficient to cause the tether to sever quickly when heat is applied. In one preferred embodiment wherein the implant to be deployed is a cerebral coil, the tether has a diameter within the range of approximately 0.001 to 0.007 inches. Of course the size of the tether can be changed to accommodate different types and sizes of other implants as necessary.

Figure 2:
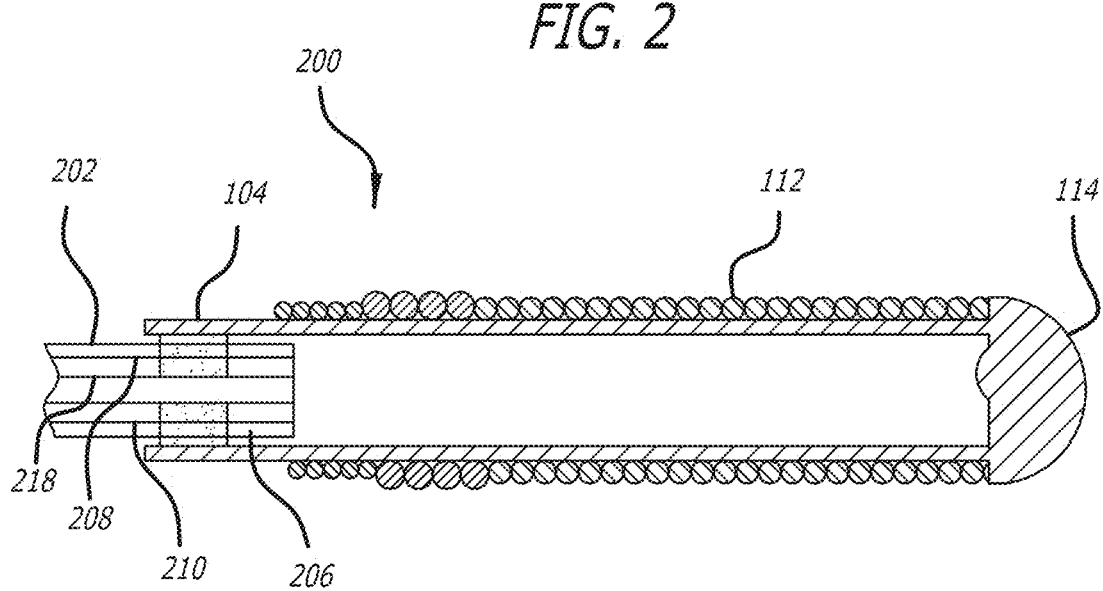
FIG. 2 illustrates a cross-sectional side view of a second embodiment of a detachment system according to the present invention.

Turning to FIG. 2, another embodiment of a detachment system of the present invention, detachment system 200, is illustrated. Detachment system 200 shares several common elements with detachment system 100. For example, the same devices usable as the implant device 112 with detachment system 100 are also usable as the implant device 112 with detachment system 200. These include, e.g., various embolic microcoils and coils. The implant device 112 has been previously described with respect to detachment system 100. As with the implant device 112, the same identification numbers are used to identify other elements/components of detachment system 100 that may correspond to elements/components of detachment system 200. Reference is made to the description of these elements in the description of detachment system 100 as that description also applies to these common elements in detachment system 200.

With detachment system 200, an interior heating element 206 is used to separate a section of a stretch resistant tube 104 and an associated implant device 112 from the detachment system 200. Detachment system 200 includes a delivery pusher 202 that incorporates a core mandrel 218. The detachment system 200 further includes a positive electrical wire 208 and a negative electrical wire 210 that extend through the lumen of the delivery pusher 202.

To form the internal heating element 206, the positive electrical wire 208 and the negative electrical wire 210 may be coupled to the core mandrel 218 of the delivery pusher 202. Preferably, the electrical wires 208, 210 are coupled to a distal portion of the core mandrel 218.

In one embodiment, the positive electrical wire 208 is coupled to a first distal location on the core wire 218, and the negative electrical wire 210 is coupled to a second distal location on the core wire 218, with the second distal location being proximal to the first distal location. In another embodiment, the configuration is reversed, i.e., the positive electrical wire 208 is coupled to the second distal location and the negative electrical wire 210 is coupled to the first distal location on the core wire 218. When the positive electrical wire 208 and the negative electrical wire 210 are coupled to the distal portion of the core mandrel 218, the distal portion of the core mandrel 218 along with the electrical wires 208, 210 forms a circuit that is the interior heating element 206.

The heater 206 increases in temperature when a current is applied from a power source (not shown) that is coupled to the positive electrical wire 208 and the negative electrical wire 210. If a greater increase in temperature/higher degree of heat is required or desired, a relatively high resistance material such as platinum or tungsten may be coupled to the distal end of the core mandrel 218 to increase the resistance of the core mandrel 218. As a result, higher temperature increases are produced when a current is applied to the heater 206 than would be produced with a lower resistance material. The additional relatively high resistance material coupled to the distal end of the core mandrel 218 may take any suitable form, such as, e.g., a solid wire, a coil, or any other shape or material as described above.

Because the heater 206 is located within the lumen of the tube-shaped tether 104, the heater 206 is insulated from the body of the patient. As a result, the possibility of inadvertent damage to the surrounding body tissue due to the heating of the heater 206 may be reduced.

When a current is applied to the heater 206 formed by the core mandrel 218, the positive electrical wire 208, and the negative electrical wire 210, the heater 206 increases in temperature. As a result, the portion of the stretch resistant tether 104 in proximity to the heater 206 severs and is detached, along with the implant device 112 that is coupled to the tether 104, from the detachment system 200.

In one embodiment of the detachment system 200, the proximal end of the stretch resistant tether 104 (or the distal end of a larger tube (not shown) coupled to the proximal end of the stretch resistant tether 104) may be flared in order to address size constraints and facilitate the assembly of the detachment system 200.

In a similar manner as with detachment system 100, energy may be stored within the system with, for example, an optional compressive spring 116 or by pre-tensioning the tether 104 during assembly as previously described. When present, the release of potential energy stored in the system operates to apply additional pressure to separate the implant device 112, and the portion of the stretch resistant tether 104 to which the implant device 112 is coupled, away from the heater 206 when the implant device 112 is deployed. This advantageously lowers the required detachment time and temperature by causing the tether 104 to sever and break.

As with detachment system 100, the distal end of the stretch resistant tether 104 of detachment system 200 may be tied or coupled to the distal end of the implant device 112, or may be melted or otherwise formed into an atraumatic distal end 114.

FIG. 4 illustrates another preferred embodiment of a detachment system 300. In many respects, the detachment system 300 is similar to the detachment system 200 shown in FIG. 2 and detachment system 100 shown in FIG. 1. For example, the detachment system 300 includes a delivery pusher 301 containing a heater 306 that detaches an implant device 302. Detachment system 300 also utilizes a tether 310 to couple the implant device 302 to the delivery pusher 301.

In the cross-sectional view of FIG. 4, a distal end of the delivery pusher 301 is seen to have a coil-shaped heater 306 that is electrically coupled to electrical wires 308 and 309. These wires 308, 309 are disposed within the delivery pusher 301, exiting at a proximal end of the delivery pusher 301 and coupling to a power supply (not shown). The tether 310 is disposed in proximity to the heater 306, having a proximal end fixed within the delivery pusher 301 and a distal end coupled to the implant device 302. As current is applied through wires 308 and 309, the heater 306 increases in temperature until the tether 310 breaks, releasing the implant device 302.

To reduce the transfer of heat from the heater 306 to the surrounding tissue of the patient and to provide electrical insulation, an insulating cover 304 is included around at least the distal end of the outer surface of the delivery pusher 301. As the thickness of the cover 304 increases, the thermal insulating properties also increase. However, increased thickness also brings increased stiffness and a greater diameter to the delivery pusher 301 that could increase the difficulty of performing a delivery procedure. Thus, the cover 304 is designed with a thickness that provides sufficient thermal insulating properties without overly increasing its stiffness.

To enhance attachment of the tether 310 to the implant device 302, the implant device 302 may include a collar member 322 welded to the implant device 302 at weld 318 and sized to fit within the outer reinforced circumference 312 of the delivery pusher 301. The tether 310 ties around the proximal end of the implant device 302 to form knot 316. Further reinforcement is provided by an adhesive 314 that is disposed around the knot 316 to prevent untying or otherwise unwanted decoupling.

In a similar manner as with detachment systems 100 and 200, energy may be stored within the system with, for example, an optional compressive spring (similar to compressive spring 116 in FIG. 1 but not shown in FIG. 4) or by axially pre-tensioning the tether 104 during assembly. In this embodiment, one end of the tether 310 is attached near the proximal end of the implant device 302 as previously described. The free end of the tether 310 is threaded through a distal portion of the delivery pusher 301 until it reaches an exit point (not shown) of the delivery pusher 301. Tension is applied to the tether 310 in order to store energy in the form of elastic deformation within the tether material by, for example, placing a pre-determined force on the free end of the tether 310 or moving the taut tether 310 a pre-determined displacement. The free end of the tether 310 is then joined to the delivery pusher 301 by, for example, tying a knot, applying adhesive, or similar methods known in the art.

When present, the release of potential energy stored in the system operates to apply additional pressure to separate the implant device 302, and the portion of the tether 310 to which the implant device 302 is coupled, away from the heater 306 when the implant device 302 is deployed. This advantageously lowers the required detachment time and temperature by causing the tether 310 to sever and break.

The present invention also provides for methods of using detachment systems such as detachment systems 100, 200, or 300. The following example relates to the use of detachment system 100, 200, or 300 for occluding cerebral aneurysms. It will, however, be appreciated that modifying the dimensions of the detachment system 100, 200, or 300 and the component parts thereof and/or modifying the implant device 112, 302 configuration will allow the detachment system 100, 200, or 300 to be used to treat a variety of other malformations within a body.

With this particular example, the delivery pusher 102, 202, or 301 of the detachment system 100, 200, or 300 may be approximately 0.010 inches to 0.030 inches in diameter. The tether 104, 310 that is coupled near the distal end of the delivery pusher 102, 202, or 301 and is coupled to the implant device 112, 302 may be 0.0002 inches to 0.020 inches in diameter. The implant device 112, 302; which may be a coil, may be approximately 0.005 inches to 0.020 inches in diameter and may be wound from 0.0005 inch to 0.005 inch wire.

If potential energy is stored within the detachment system 100, 200, or 300, the force used to separate the implant device 112, 302 typically ranges up to 250 grams.

The delivery pusher 102, 202, or 301 may comprise a core mandrel 218 and at least one electrically conductive wire 108, 110, 208, 210, 308, or 309. The core mandrel 218 may be used as an electrical conductor, or a pair of conductive wires may be used, or a bipolar wire may be used as previously described.

Figure 8:
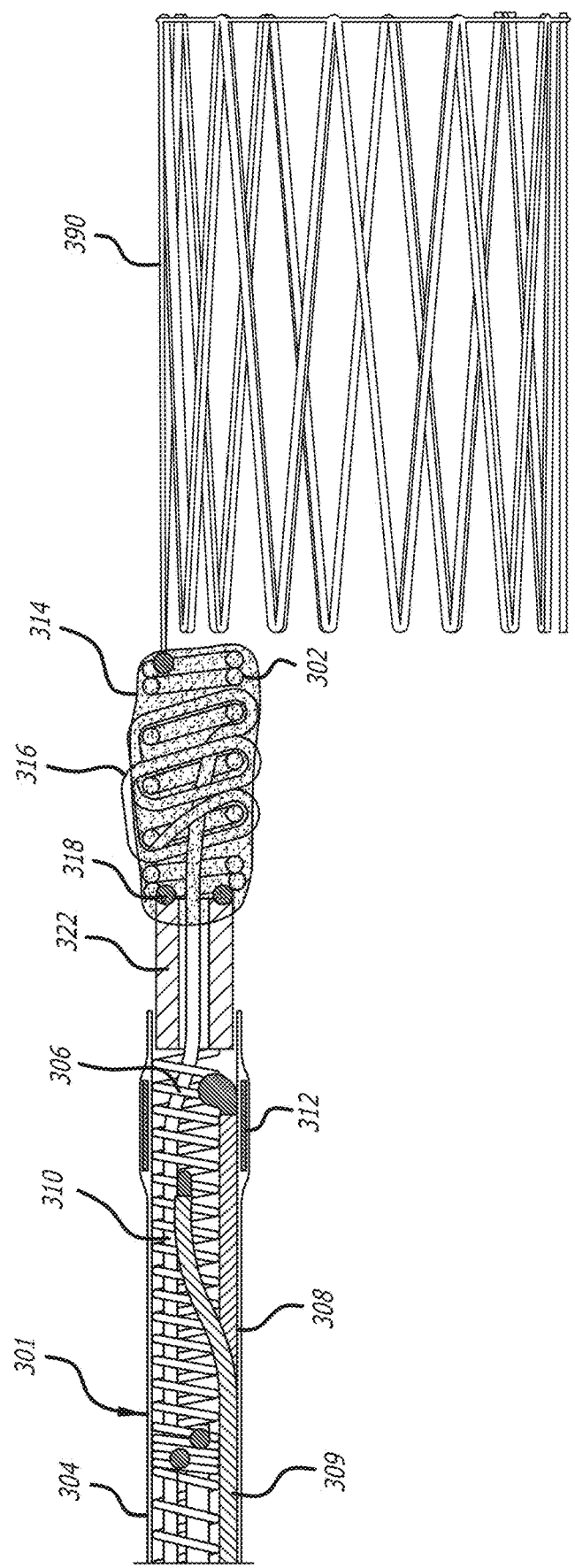
FIG. 8 illustrates a cross-sectional side view of a detachment system including a stent according to the present invention.

Although the detachment systems 100, 200, and 300 have been illustrated as delivering a coil, other implant devices are contemplated in the present invention. For example, FIG. 8 illustrates the detachment system 300 as previously described in FIG. 4 having an implant that is a stent 390. This stent 390 could similarly be detached by a similar method as previously described in regards to the detachment systems 100, 200, and 300. In a further example, the detachment systems 100, 200, or 300 may be used to deliver a filter, mesh, scaffolding or other medical implant suitable for delivery within a patient.

Figure 7:
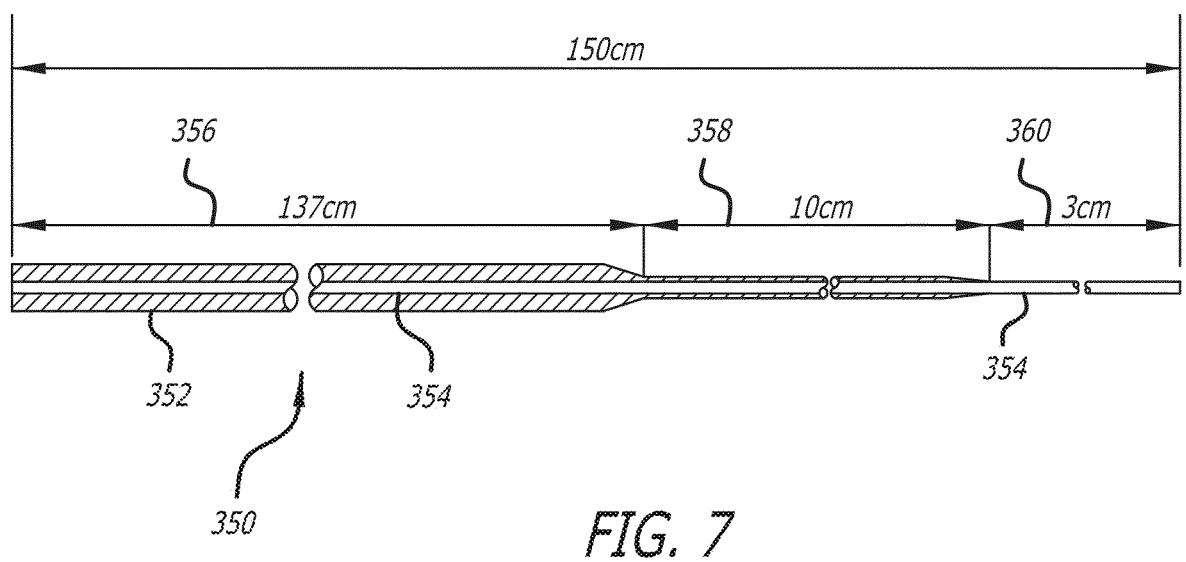
FIG. 7 illustrates a cross-sectional side view of radiopaque layers of a detachment system according to the present invention.

FIG. 7 presents an embodiment of a delivery pusher 350, which could be used in any of the embodiments as delivery pusher 102, 202, or 301, which includes radiopaque materials to communicate the position of the delivery pusher 350 to the user. Specifically, the radiopaque marker material is integrated into the delivery pusher 350 and varied in thickness at a desired location, facilitating easier and more precise manufacturing of the final delivery pusher 350.

Prior delivery pusher designs, such as those seen in U.S. Pat. No. 5,895,385 to Guglielmi, rely on high-density material such as gold, tantalum, tungsten, or platinum in the form of an annular band or coil. The radiopaque marker is then bonded to other, less dense materials, such as stainless steel, to differentiate the radiopaque section. Since the radiopaque marker is a separate element placed at a specified distance (often about 3 cm) from the tip of the delivery pusher, the placement must be exact or the distal tip of the delivery pusher 350 can result in damage to the aneurysm or other complications. For example, the delivery pusher 350 may be overextended from the microcatheter to puncture an aneurysm. Additionally, the manufacturing process to make a prior delivery pusher can be difficult and expensive, especially when bonding dissimilar materials.

The radiopaque system of the present invention overcomes these disadvantages by integrating a first radiopaque material into most of the delivery pusher 350 while varying the thickness of a second radiopaque material, thus eliminating the need to bond multiple sections together. As seen in FIG. 7, the delivery pusher 350 comprises a core mandrel 354 (i.e. the first radiopaque material), preferably made from radiopaque material such as tungsten, tantalum, platinum, or gold (as opposed to the mostly radiolucent materials of the prior art designs such as steel, Nitinol, and Elgiloy).

The delivery pusher 350 also includes a second, outer layer 352, having a different radiopaque level. Preferably, outer layer 352 is composed of a material having a lower radiopaque value than the core mandrel 354, such as Elgiloy, Nitinol, or stainless steel (commercially available from Fort Wayne Metals under the trade name DFT). In this respect, both the core mandrel 354 and the outer layer 352 are visible and distinguishable from each other under fluoroscopy. The outer layer 352 varies in thickness along the length of the delivery pusher 350 to provide increased flexibility and differentiation in radio-density. Thus the thicker regions of the outer layer 352 are more apparent to the user than the thinner regions under fluoroscopy.

The transitions in thickness of the outer layer 352 can be precisely created at desired locations with automated processes such as grinding, drawing, or forging. Such automated processes eliminate the need for hand measuring and placement of markers and further eliminates the need to bond a separate marker element to other radiolucent sections, thus reducing the manufacturing cost and complexity of the system.

In the present embodiment, the delivery pusher 350 includes three main indicator regions of the outer layer 352. A proximal region 356 is the longest of the three at 137 cm, while a middle region 358 is 10 cm and a distal region 360 is 3 cm. The length of each region can be determined based on the use of the delivery pusher 350. For example, the 3 cm distal region 360 may be used during a coil implant procedure, as known in the art, allowing the user to align the proximal edge of the distal region 360 with a radiopaque marker on the microcatheter within which the delivery pusher 350 is positioned. The diameter of each of the regions depends on the application and size of the implant. For a typical cerebral aneurysm application for example, the proximal region 356 may typically measure 0.005-0.015 inches, the middle region 358 may typically measure 0.001-0.008 inches, while the distal region 360 may typically measure 0.0005-0.010 inches. The core mandrel 354 will typically comprise between about 10-80% of the total diameter of the delivery pusher 350 at any point.

Alternately, the delivery pusher 350 may include any number of different regions greater than or less than the three shown in FIG. 7. Additionally, the radiopaque material of the core mandrel 354 may only extend partially through the delivery pusher 350. For example, the radiopaque material could extend from the proximal end of the core mandrel 354 to three centimeters from the distal end of the delivery pusher 350, providing yet another predetermined position marker visible under fluoroscopy.

In this respect, the regions 356, 358, and 360 of delivery pusher 350 provide a more precise radiopaque marking system that is easily manufactured, yet is readily apparent under fluoroscopy. Further, the increased precision of the markers may decrease complications relating to improper positioning of the delivery pusher during a procedure.

In operation, the microcatheter is positioned within a patient so that a distal end of the microcatheter is near a target area or lumen. The delivery pusher 350 is inserted into the proximal end of the microcatheter and the core mandrel 354 and outer layer 352 are viewed under fluoroscopy. The user aligns a radiopaque marker on the microcatheter with the beginning of the distal region 360, which communicates the location of the implant 112, 302 relative to the tip of the microcatheter.

In some situations, for example, small aneurysms where there may be an elevated risk of vessel damage from the stiffness of the delivery pusher 350, the user may position the proximal end of the implant slightly within the distal end of the microcatheter during detachment. The user then may push the proximal end of the implant 112, 302 out of the microcatheter with the next coil, an adjunctive device such as guidewire, or the delivery pusher 102, 202, 301, or 350. In another embodiment, the user may use the radiopaque marking system to locate the distal end of the delivery pusher outside the distal end of the microcatheter.

Once the implant device 112, 302 of the detachment system 100, 200, or 300 is placed in or around the target site, the operator may repeatedly reposition the implant device 112, 302 as necessary or desired.

When detachment of the implant device 112, 302 at the target site is desired, the operator applies energy to the heater 106, 206, or 306 by way of the electrical wires 108, 110, 208, 210, 308, or 309. The electrical power source for the energy may be any suitable source, such as, e.g., a wall outlet, a capacitor, a battery, and the like. For one aspect of this method, electricity with a potential of approximately 1 volt to 100 volts is used to generate a current of 1 milliamp to 5000 milliamps, depending on the resistance of the detachment system 100, 200, or 300.

One embodiment of a connector system 400 that can be used to electrically couple the detachment system 100, 200, or 300 to the power source is shown in FIG. 6. The connector system 400 includes an electrically conductive core mandrel 412 having a proximal end surrounded by an insulating layer 404. Preferably the insulating layer 404 is an insulating sleeve such as a plastic shrink tube of polyolefin, PET, Nylon, PEEK, Teflon, or polyimide. The insulating layer 404 may also be a coating such as polyurethane, silicone, Teflon, paralyene. An electrically conductive band 406 is disposed on top of the insulating layer 404 and secured in place by molding bands 414, adhesive, or epoxy. Thus, the core mandrel 412 and the conductive band 406 are electrically insulated from each other. The conductive band 406 is preferably composed of any electrically conductive material, such as silver, gold, platinum, steel, copper, conductive polymer, conductive adhesive, or similar materials, and can be a band, coil, or foil. Gold is especially preferred as the conductive material of the conductive band 406 because of the ability of gold to be drawn into a thin wall and its ready availability. The core mandrel 412 has been previously described and may be plated with, for example, gold, silver, copper, or aluminum to enhance its electrical conductivity.

The connector system 400 also includes two electrical wires 408 and 410 which connect to the conductive band 406 and core member 412, respectively, and to a heating element at the distal end of a delivery system such as those described in FIGS. 1, 2, and 4 (not shown in FIG. 6). These wires 408 and 410 are preferably connected by soldering, brazing, welding, laser bonding, or conductive adhesive, or similar techniques.

Once the user is ready to release the implant 112, 302 within the patient, a first electrical clip or connector from a power source is connected to a non-insulated section 402 of the core mandrel 412 and a second electrical clip or connector from the power source is connected to the conductive band 406. Electrical power is applied to the first and second electrical clips, forming an electrical circuit within the detachment system 100, 200, or 300, causing the heater 106, 206, or 306 to increase in temperature and sever the tether 104, 310.

Once the detachment system 100, 200, or 300 is connected to the power source the user may apply a voltage or current as previously described. This causes the heater 106, 206, or 306 to increase in temperature. When heated, the pre-tensioned tether 104, 310 will tend to recover to its unstressed (shorter) length due to heat-induced creep. In this respect, when the tether 104, 310 is heated by the heater 106, 206, or 306; its overall size shrinks. However, since each end of the tether 104, 310 is fixed in place as previously described, the tether 104, 310 is unable to shorten in length, ultimately breaking to release the implant device 112, 302.

Because there is tension already within the system in the form of a spring 116 or deformation of the tether material 104, 310; the amount of shrinkage required to break the tether 104, 310 is less than that of a system without a pre-tensioned tether. Thus, the temperature and time required to free the implant device 112, 302 is lower.

Figure 5:
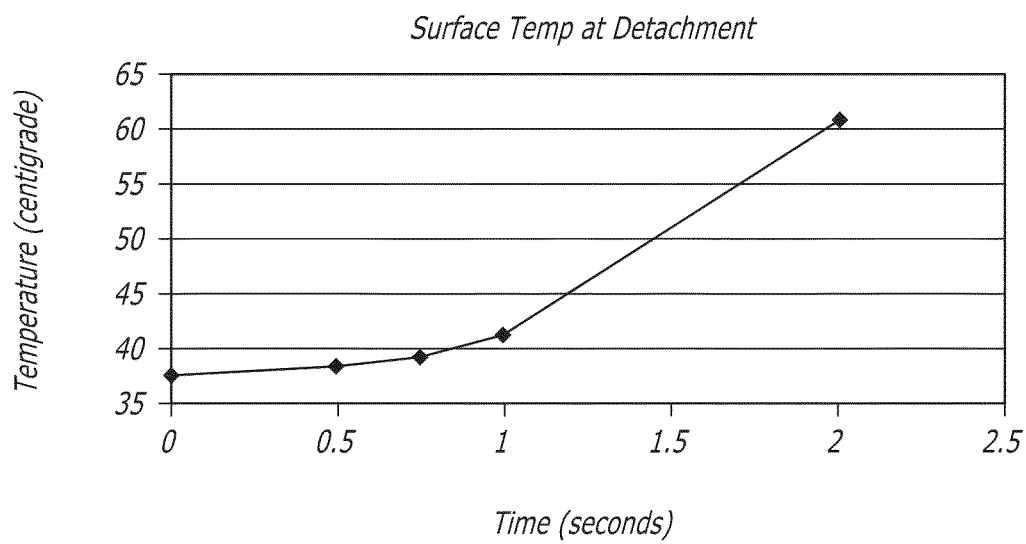
FIG. 5 illustrates example temperature data of the surface of a detachment system according to the present invention.

FIG. 5 is a graph showing the temperatures at the surface of the PET cover 304 of the detachment system 300. As can be seen, the surface temperature of the detachment system 300 during detachment does not vary linearly with time. Specifically, it only takes just under 1 second for the heat generated by the heating coil 306 to penetrate the insulating cover 304. After 1 second, the surface temperature of the insulating cover 304 dramatically increases. Although different outer insulating material may slightly increase or decrease this 1-second surface temperature window, the necessarily small diameter of the detachment system 100, 200, or 300 prevents providing a thick insulating layer that may more significantly delay a surface temperature increase.

It should be understood that the embodiments of the detachment system 100, 200, or 300 include a variety of possible constructions. For example, the insulating cover 304 may be composed of Teflon, PET, polyamide, polyimide, silicone, polyurethane, PEEK, or materials with similar characteristics. In the embodiments 100, 200, or 300 the typical thickness of the insulating cover is 0.0001-0.040 inches. This thickness will tend to increase when the device is adapted for use in, for example, proximal malformations, and decrease when the device is adapted for use in more distal, tortuous locations such as, for example, cerebral aneurysms.

In order to minimize the damage and possible complications caused by such a surface temperature increase, the present invention detaches the implant device 112, 302 before the surface temperature begins to significantly increase. Preferably, the implant device 112, 302 is detached in less than a second, and more preferably, in less than 0.75 seconds. This prevents the surface temperature from exceeding 50° C. (122° F.), and more preferably, from exceeding 42° C. (107° F.).

Once the user attempts to detach the implant device 112, 302, it is often necessary to confirm that the detachment has been successful. The circuitry integrated into the power source may be used to determine whether or not the detachment has been successful. In one embodiment of the present invention an initial signaling current is provided prior to applying a detachment current (i.e. current to activate the heater 106, 206, or 306 to detach an implant 112, 302). The signaling current is used to determine the inductance in the system before the user attempts to detach the implant and therefore has a lower value than the detachment current, so as not to cause premature detachment. After an attempted detachment, a similar signaling current is used to determine a second inductance value that is compared to the initial inductance value. A substantial difference between the initial inductance and the second inductance value indicates that the implant 112, 302 has successfully been detached, while the absence of such a difference indicates unsuccessful detachment. In this respect, the user can easily determine if the implant 112, 302 has been detached, even for delivery systems that utilize nonconductive temperature sensitive polymers to attach an implant, such as those seen in FIGS. 1, 2, and 4.

In the following description and examples, the terms "current" and "electrical current" are used in the most general sense and are understood to encompass alternating current (AC), direct current (DC), and radiofrequency current (RF) unless otherwise noted. The term "changing" is defined as any change in current with a frequency above zero, including both high frequency and low frequency. When a value is measured, calculated and/or saved, it is understood that this may be done either manually or by any known electronic method including, but not limited to, an electronic circuit, semiconductor, EPROM, computer chip, computer memory such as RAM, ROM, or flash; and the like. Finally, wire windings and toroid shapes carry a broad meaning and include a variety of geometries such as circular, elliptical, spherical, quadrilateral, triangular, and trapezoidal shapes.

When a changing current passes through such objects as wire windings or a toroid, it sets up a magnetic field. As the current increases or decreases, the magnetic field strength increase or decreases in the same way. This fluctuation of the magnetic field causes an effect known as inductance, which tends to oppose any further change in current. Inductance (L) in a coil wound around a core is dependant on the number of turns (N), the cross-sectional area of the core (A), the magnetic permeability of the core (μ), and length of the coil (I) according to equation 1 below:

$$L = \frac{.4\pi N^2 A \mu}{l} \quad \text{Equation 1}$$

Figure 3A:
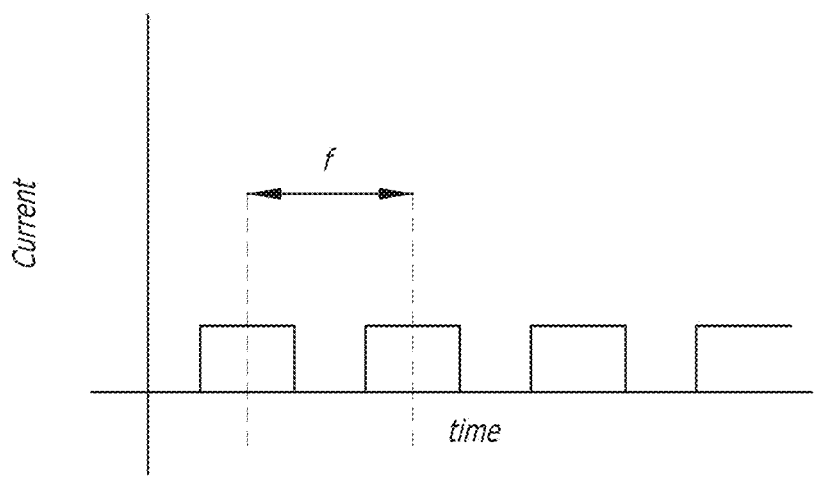
FIG. 3A illustrates example direct signaling current according to the present invention.
Figure 3B:
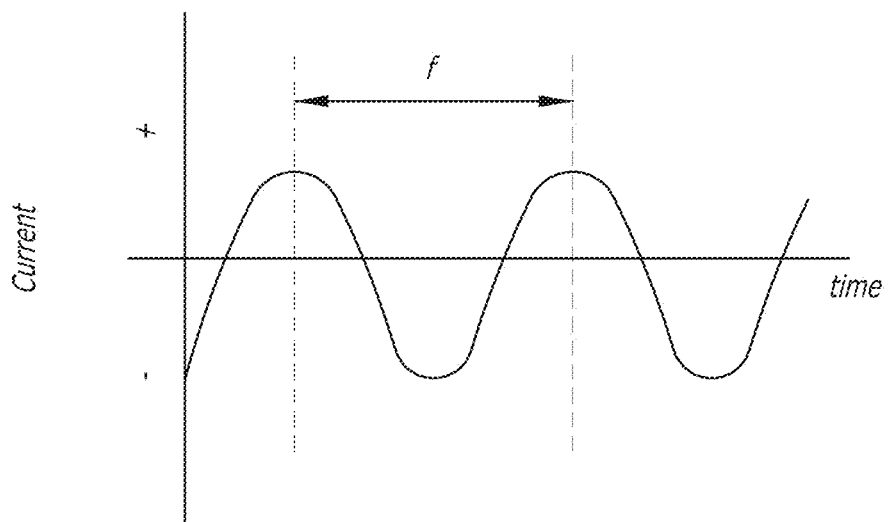
FIG. 3B illustrates example alternating signaling current according to the present invention.

The heater 106 or 306 is formed from a wound coil with proximal and distal electrically conductive wires 108, 110, 308, or 309 attached to a power source. The tether 104, 310 has a magnetic permeability μ1 and is positioned through the center of the resistive heater, having a length I, cross sectional area A, and N winds, forming a core as described in the previous equation. Prior to detachment, a changing signaling current i1, such as the waveforms shown in FIGS. 3A and 3B, with frequency f1, is sent through the coil windings. This signaling current is generally insufficient to detach the implant. Based on the signaling current, the inductive resistance XL (i.e. the electrical resistance due to the inductance within the system) is measured by an electronic circuit such as an ohmmeter. The initial inductance of the system L1 is then calculated according to the formula:

$$L_1 = \frac{X_L}{2\pi f_1} \quad \text{Equation 2}$$

This initial value of the inductance L1 depends on the magnetic permeability μ1 of the core of the tether 104, 310 according to Equation 1, and is saved for reference. When detachment is desired, a higher current and/or a current with a different frequency than the signaling current is applied through the resistive heater coil, causing the tether 104, 310 to release the implant 112, 302 as previously described. If detachment is successful, the tether 104, 310 will no longer be present within the heater 106, 306 and the inside of the heater 106, 306 will fill with another material such as the patient's blood, contrast media, saline solution, or air. This material now within the heater core will have a magnetic permeability μ2 that is different than the tether core magnetic permeability μ1.

A second signaling current and frequency f2 is sent through the heater 106, 306 and is preferably the same as the first signaling current and frequency, although one or both may be different without affecting the operation of the system. Based on the second signaling current, a second inductance L2 is calculated. If the detachment was successful, the second inductance L2 will be different (higher or lower) than the first inductance L1 due to the difference in the core magnetic permeabilities μ1 and μ2. If the detachment was unsuccessful, the inductance values should remain relatively similar (with some tolerance for measurement error). Once detachment has been confirmed by comparing the difference between the two inductances, an alarm or signal can be activated to communicate successful detachment to the user. For example, the alarm might include a beep or an indicator light.

Preferably, the delivery system 100, 300 used according to this invention connects to a device that automatically measures inductance at desired times, performs required calculations, and signals to the user when the implant device has detached from the delivery catheter. However, it should be understood that part or all of these steps can be manually performed to achieve the same result.

The inductance between the attached and detached states can also preferably be determined without directly calculating the inductance. For example, the inductive resistance XL can be measured and compared before and after detachment. In another example, the detachment can be determined by measuring and comparing the time constant of the system, which is the time required for the current to reach a predetermined percentage of its nominal value. Since the time constant depends on the inductance, a change in the time constant would similarly indicate a change in inductance.

The present invention may also include a feedback algorithm that is used in conjunction with the detachment detection described above. For example, the algorithm automatically increases the detachment voltage or current automatically after the prior attempt fails to detach the implant device. This cycle of measurement, attempted detachment, measurement, and increased detachment voltage/current continues until detachment is detected or a predetermined current or voltage limit is attained. In this respect, a low power detachment could be first attempted, followed automatically by increased power or time until detachment has occurred. Thus, battery life for a mechanism providing the detachment power is increased while the average coil detachment time is greatly reduced.

Figure 9:
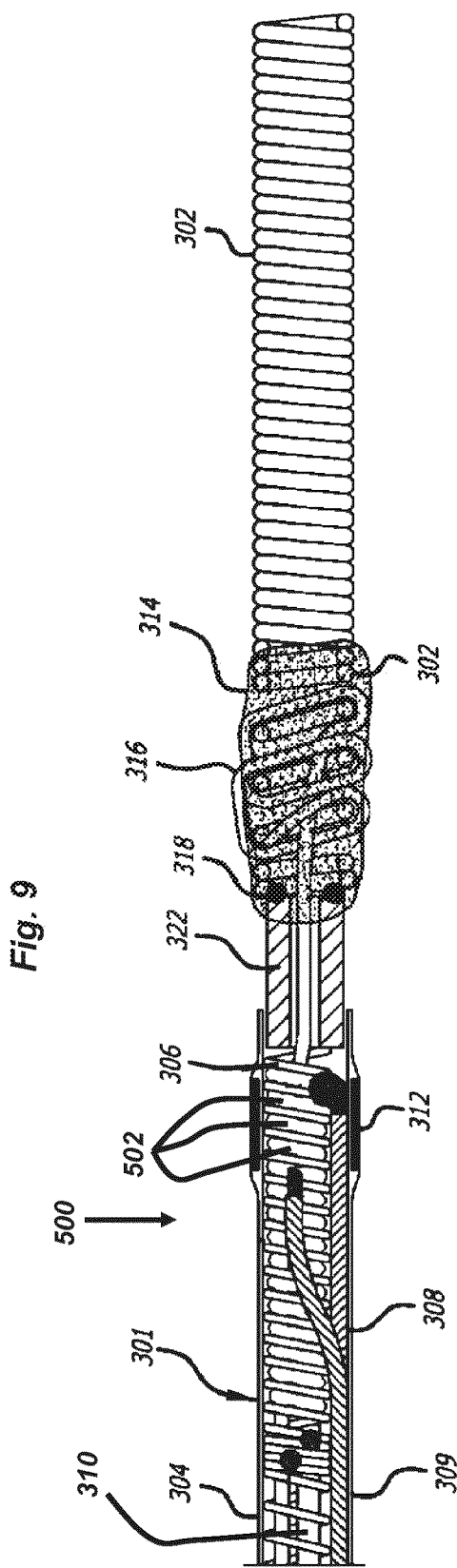
FIG. 9 illustrates a side view of a implant device according to the present invention.
Figure 10:
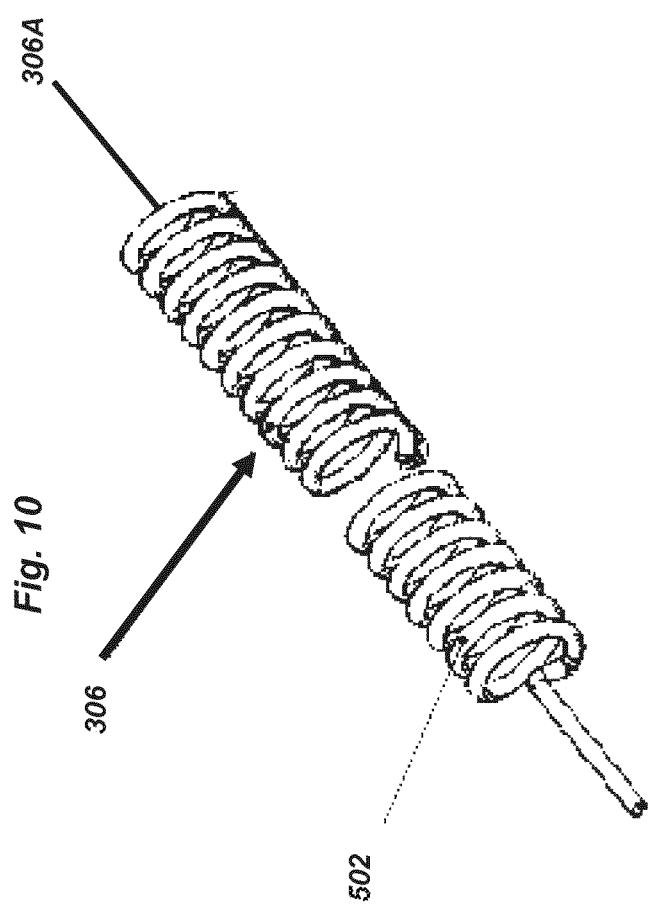
FIG. 10 illustrates a perspective view of a coil and spacer of the delivery system of FIG. 9.

Referring now to FIGS. 9 and 10, there is shown an embodiment of a delivery system 500 for use with the present invention that includes a detachment detection capability. The delivery system 500 operates under the principle that electrical current passing through a coil held in an expanded, open gap configuration will encounter more resistance than electrical current passing through a coil in a contracted, closed gap configuration. In the expanded configuration, the electrical current must follow the entire length of the coiled wire. In the contracted configuration, the electrical current can bridge the coils and travel in a longitudinal direction.

The delivery system 500 is generally similar to the previously described detachment system 300 of the present invention seen in FIG. 4, including a delivery pusher 301, containing a heater coil 306 that detaches an implant device 302. The detachment system 500 similarly utilizes a tether 310 to couple the implant device 302 to the delivery pusher 301.

The heater coil 306 is preferably a resistance-type heater having a plurality of loops 306A as seen in FIG. 10 that connects to a voltage source through a connector system at the proximal end of the delivery pusher 301, such as the connector system 400 described in FIG. 6.

The delivery system 500 also includes a heater coil expander 502 that serves two functions. First, it expands the heater coil 306 such that the heater coil 306 maintains a friction-fit attachment to the inside of the insulating cover 309, thereby connecting the two. Second, the heater coil expander 502 expands the heater coil 306 in such a manner that electricity is forced to flow around each individual loop 306A of the coil 306 in order to maximize the resistance of the coil 306.

Maximizing the coil resistance not only serves to heat the coil 306 when voltage is passed through, it also sets an initial value (or "normal" value) for the resistance provided by the coil 306, which can be used to compare a changed resistance state, indicating detachment of the implant 302. Hence, the heater coil expander 502 must also be capable of undergoing change when subjected to heat. In this regard, the heater coil expander 502 may be made of any suitable sturdy material capable of holding the heater coil 306 in an expanded, biased state while also being capable of melting or being otherwise reduced by the heat of the heater coil 306 in order to yield to the bias of the heater coil 306 to return to an unbiased state. Examples of acceptable materials include, but are not limited to, polymers and monofilament.

The heater coil expander 502 shown in FIGS. 9 and 10 operates by longitudinally, or radially and longitudinally, expanding a heater coil 306 which is normally a closed gap coil in a relaxed state. In other words, the individual loops 306A contact each other when the' heater coil 306 is not stretched or radially expanded. Preferably, the heater coil expander 502 may have a coiled shape, similar to the heater coil 306 and as seen in FIG. 10. Alternately, the heater coil expander may have a continuous, tubular shape with helical ridges similar to the individual coil shapes of the expander 502 in FIG. 10. It should be understood that a variety of different expander shapes that expand the loops or coils 306A of the heater coil 306 from each other.

Preferably the power source (previously described in this embodiment and connected to the connector system 400) also includes a measuring instrument for measuring the resistance of the heater coil 306. In this respect, the power source (preferably located in a hand-sized unit) includes an indicator that communicates when a change in resistance has occurred and therefore when detachment of the implant has occurred.

Figure 11:
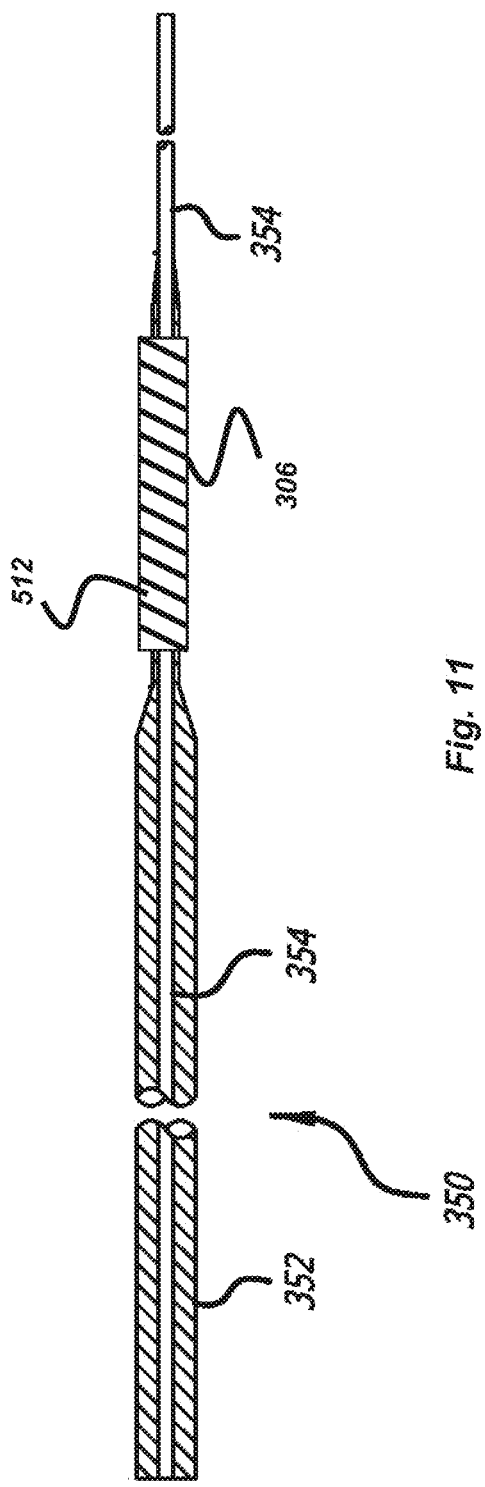
FIG. 11 illustrates a side view of a pusher of the delivery system of according to the present invention.
Figure 12:
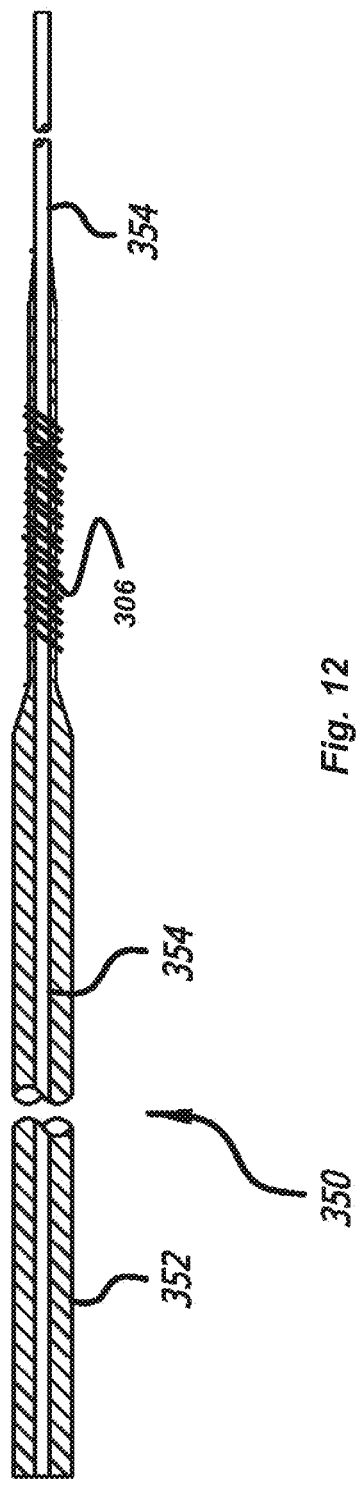
FIG. 12 illustrates a side view of the pusher of the delivery system of FIG. 11.

An alternative embodiment of the heater coil expander 512 is shown in FIGS. 10 and 11. The heater coil expander 512 operates in conjunction with the heater coil 306 so that the heater loops are in an open gap state (FIG. 10), and a pusher 350, as previously described in FIG. 7, that conducts electricity. The heater coil 306 is sized to snugly fit around the pusher 350 in a contracted state. The heater coil expander 512 operates to separate the heater coil 306 from the pusher 350, electrically isolating the heater coil 306 therefrom. As the heat from the heater coil 306 melts or otherwise reduces or degrades the heater coil expander 512, the heater coil 306 resumes a contracted state (i.e., reduced diameter configuration), making electrical, if not physical, contact with the pusher 350 (FIG. 11). In this respect the individual loops are shortened, significantly reducing the resistance of the circuit and thereby indicating detachment has occurred.

Another alternative embodiment of the present invention, the heater coil expander 502 may be sized to expand the heater coil 306 against the conductive reinforcement circumference 312 (shown in FIG. 9). Hence, when the coil 306 is in its initial expanded position, the electrically conductive reinforcement circumference 312 maintains a low initial resistance that is registered by the controller for the circuit (i.e., the measurement device of the power source).

When the heater coil 306 is energized, the initial resistance is noted and the heater coil expander 306 melts, degrades or otherwise reduces. The heater coil 306 then contracts, releasing the attachment tube 512 (and the rest of the implant 510) and the heater coil 522a is no longer shorted out by the reinforcement circumference 312. Thus, the circuit experiences a change in resistance as the electrical current must travel through each of the individual loops 524a. This increase in resistance signifies the implant 302 is detached.

FIGS. 13-16 illustrate another preferred embodiment of a delivery system 600 according to the present invention. For illustrative purposes, it should be noted that the outer body of the system 600 is not shown. The delivery system 600 is generally similar to some of the previously described embodiments, in that it includes a tether 606 that secures an implantable device 612 to the delivery system 600 and a heater coil 604 that causes the tether 606 to break, thereby releasing the implantable device 612.

However, as seen in these Figures, the heater coil 604 is sized with a diameter that is much smaller than previous embodiments. More specifically, the heater coil 604 preferably has an internal passage that is only slightly larger in diameter than the outer diameter of the tether 606. In other words, the internal diameter of the heater coil 604 is substantially the same as the outer diameter of the tether 604.

According to one embodiment, the internal passage of the heating coil 604 solely contains the tether 606. According to another embodiment, the diameter of the internal passage may be large enough for only the tether 606 to pass through. In another embodiment, the diameter may be large enough for only the tether and other components, such as support mandrel 611 or electrical wires 608 and 610. In either case, at least a portion of the internal diameter of the heater coil 604 maintains a close proximity to the tether 606, allowing the tether 606 to pass through once.

Additionally, the heater coil 604 preferably includes a smaller diameter region 604A which is positioned closer to the tether 606 than the remaining portions of the coil 604. In this respect, the region 604A can more efficiently transfer heat to the tether 606 and therefore break the tether with an otherwise lower temperature than without the region 604A. Providing a lower temperature reduces the risk of damaging the patient's tissue surrounding the system 600. In a specific example, the heater coil 604 has an internal diameter of about 0.007 inch and an internal diameter of about 0.005 inch at region 604A while the tether 606 has an external diameter of about 0.004 inch.

As in previously described embodiments, the heater coil 604 may be composed of a coiled heating element wire. However, it should be understood that other heater configurations are possible, such as a solid, conducting tube or a wire arranged in a non-coiled shape, such as a wave or undulating pattern that forms an overall tubular shape (that may not completely surround the tether 606).

Both ends of the tether 606 are preferably secured to an outer structural coil 602 of the delivery device 600. For example, the ends of the tether 606 can be tied, glued (e.g., with U.V. cured adhesive), welded or clamped. It should be understood that the ends of the tether 606 can be secured at almost any location along the length of the structural coil 602, as long as those locations allow at least a portion of the tether 606 to pass through the heater coil 604. For example, both ends of the tether 606 can be secured proximal to the heater coil 604. In another example, one end of the tether can be secured proximal to heater coil 604 and another end can be secured distal to the heater coil 604.

Figure 13:
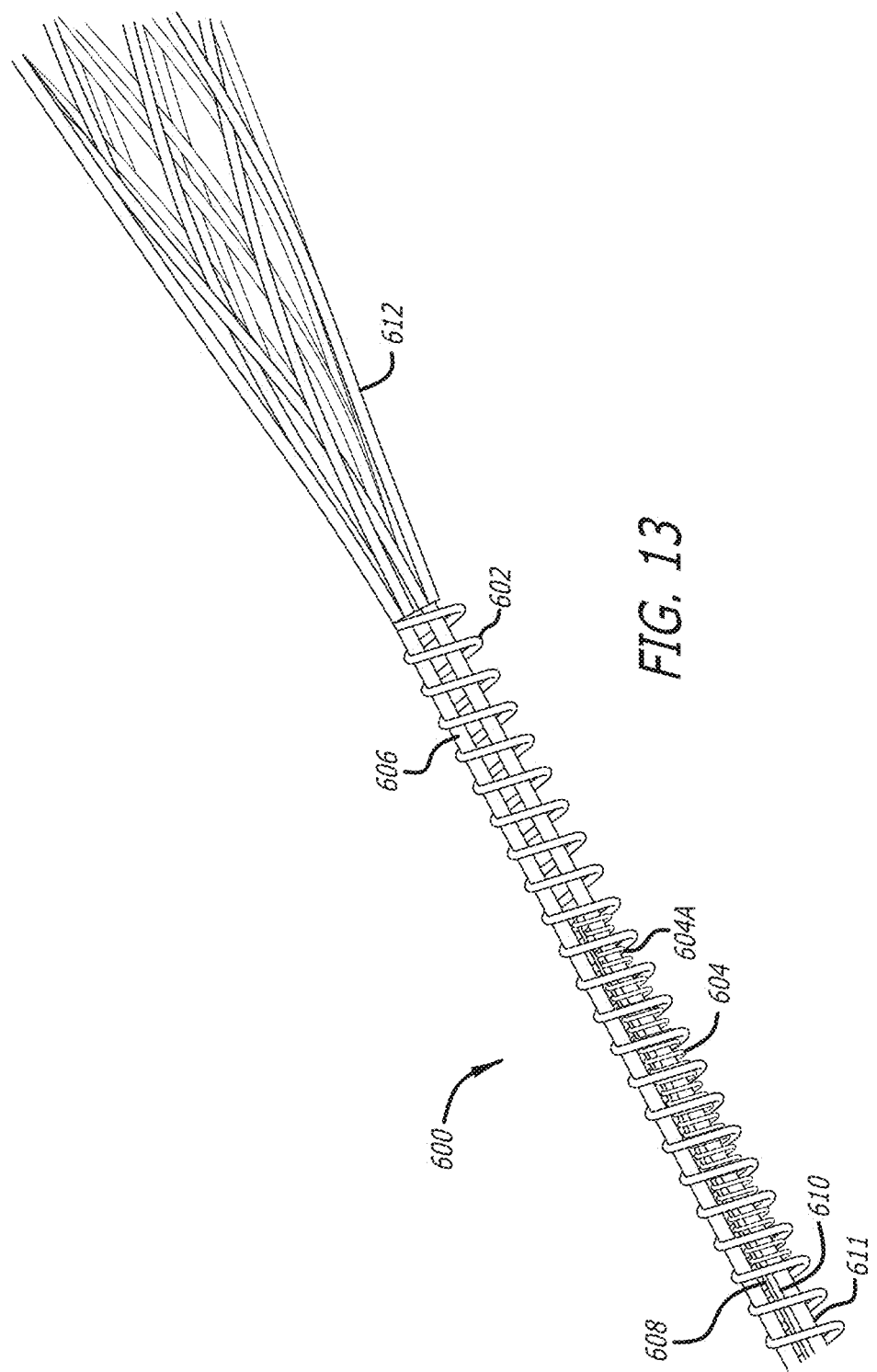
FIG. 13 illustrates a perspective view of a delivery system according to the present invention.
Figure 14:
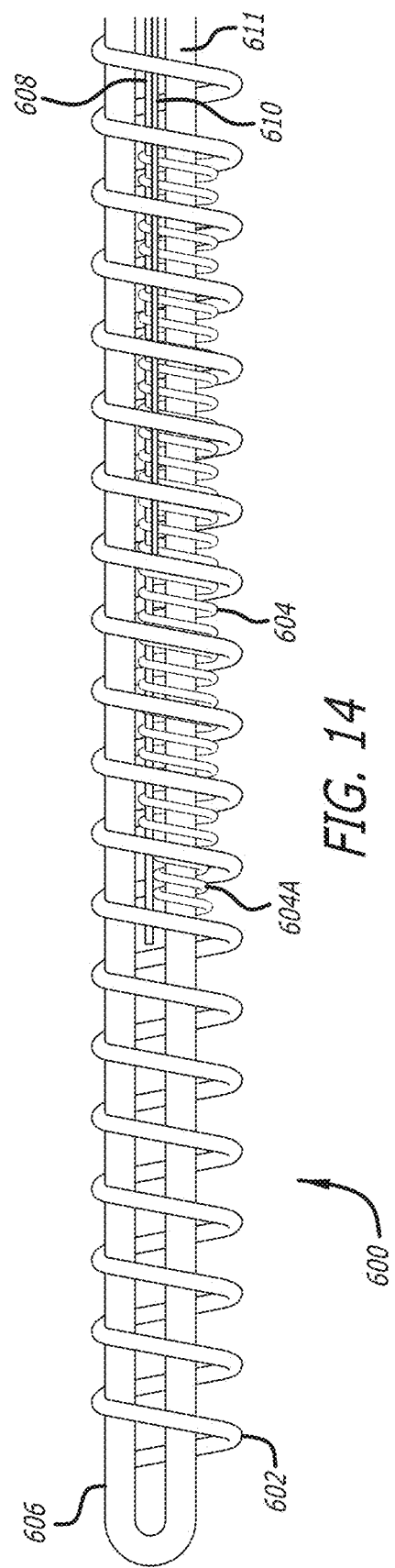
FIG. 14 illustrates a side view of the delivery system of FIG. 13.
Figure 15:
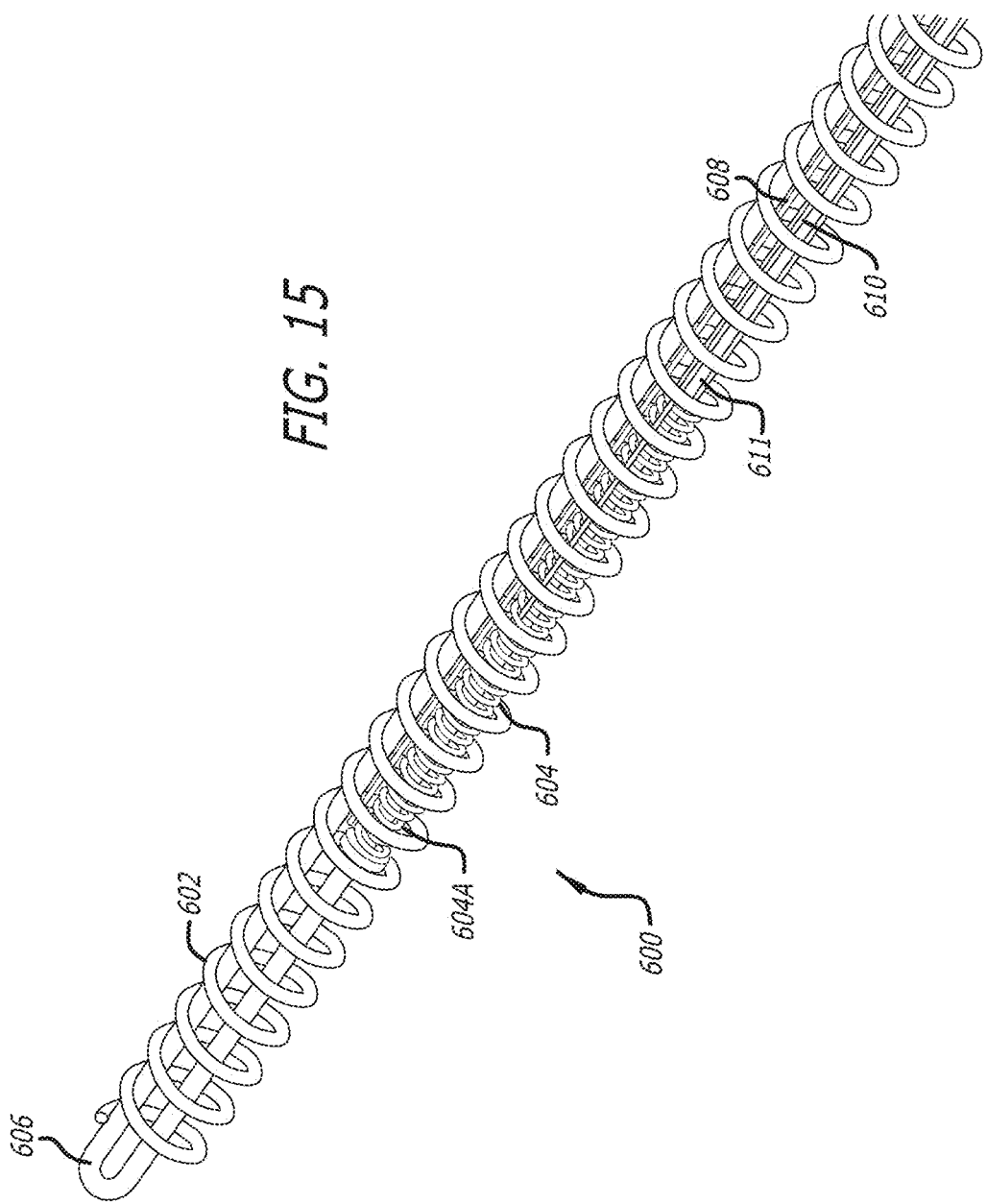
FIG. 15 illustrates a perspective view of the delivery system of FIG. 13.
Figure 16:
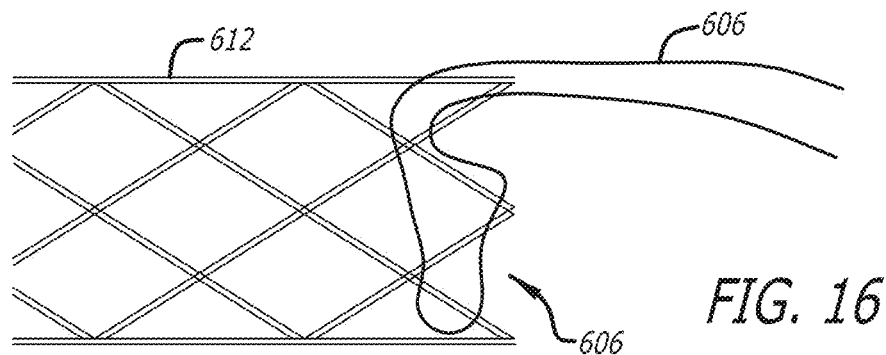
FIG. 16 illustrates a side view of the tether and implant device of FIG. 13.
Figure 17:
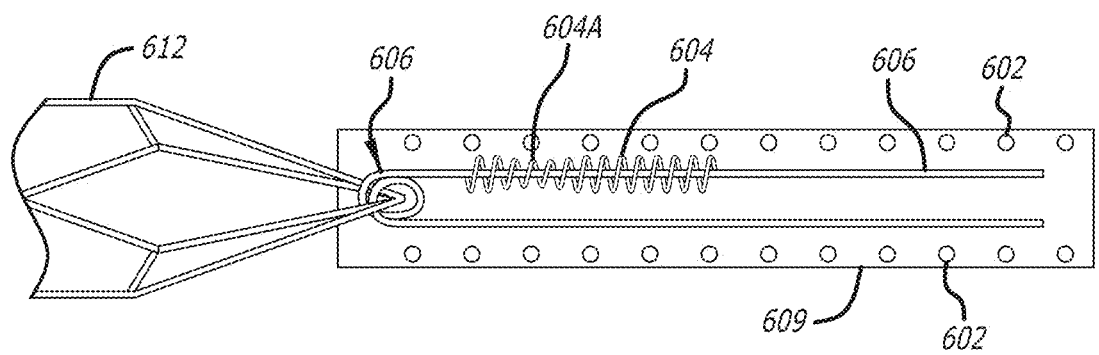
FIG. 17 illustrates a side view of the delivery system of FIG. 13.

As seen in FIGS. 13, 16, and 17, the tether 606 preferably passes through openings, cells, loops or other structures of the implantable device 612. For example, the tether 606 may pass through cells of a stent. As seen in FIG. 16, the tether 606 can pass through multiple cells of the device 612 and is maintained under tension as seen in FIGS. 13 and 17. The tension of the tether 606 keeps the device 612 in a compressed state (i.e., compressed in diameter) and abutted to the distal end of the system 600 (e.g., the distal end of the outer body member 609). In this respect, when the tether 606 is broken by the heater coil 604, the tether 606 unwraps from the device 612 and stays with the delivery system 600, not the device 612. Hence, the tether 606 does not remain in the patient to potentially cause unwanted complications.

As with previously described embodiments, the delivery system 600 is connectable to a selectively actuated power supply (e.g., via a button on a handle of the delivery device 600). Wires 608 and 610 deliver electric current to the heater coil 604 at a desired time, causing the coil 604 to heat and thereby break the tether 606.

Preferably, the heater coil 604 is supported within the delivery system 600 by a support mandrel 611 (best seen in FIG. 15) that extends along a length of the system 600. Preferably, the support mandrel 611 is secured to the heater coil 604 by welding, adhesive or a mechanical interlocking arrangement (not shown). The proximal end of the support mandrel 611 is preferably attached to a core wire or delivery pusher (e.g., pusher 350 described in other embodiments in this specification).

The outer coil 602 provides support to the delivery system and can be positioned on the inside of a lumen of the delivery system body 609 (see FIG. 17). Alternately, this coil 602 can be positioned between material layers of the delivery system body 609 (not shown) or otherwise embedded in the material of the delivery system body 609.

In operation, a distal end of the delivery system 600 is positioned at a target location within a patient. When the implantable device 612 (e.g., catheter, valve or microcoil) has achieved a desired position, the user provides electric current to the heater coil 604 (e.g., via a button on the delivery device 600). The heater coil 604, including section 604A, increases in temperature, causing the tether 606 to break. The tether 606, previously under tension, passes through the cells or attachment points of the implantable device 612 releasing the device 612 from the delivery system 600. The delivery system 600 can then be removed from the patient, along with the attached tether 606.

Figure 18:
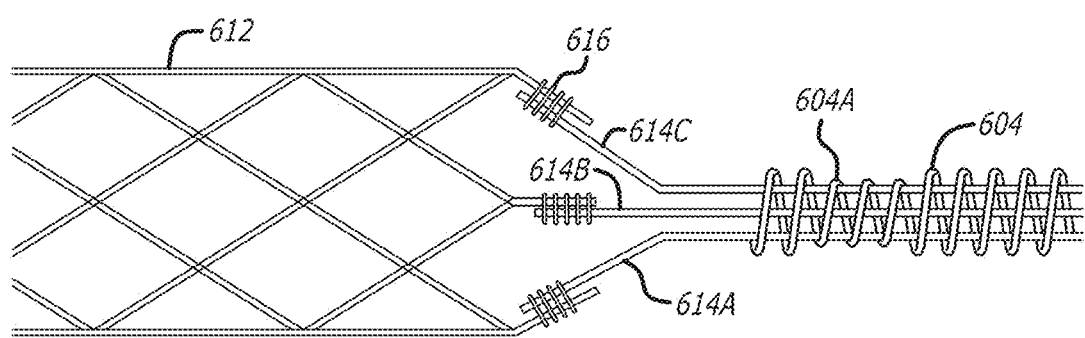
FIG. 18 illustrates a side view of an alternate tether arrangement for the delivery system of FIG. 13.

It should be understood that other tether arrangements are possible according to the present invention. For example, FIG. 18 illustrates the use of three tethers 614A, 614B and 614C which attach to different locations on the device 612. Preferably, these tethers 614A, 614B and 614C have a smaller diameter than the previously described tether 606. In the present preferred embodiment, the tethers 614A, 614B and 614C are tied to the device 612 at knots 616. However, adhesives, clamps and other attachment arrangements are also possible. While not shown in the Figures, each tether 614A, 614B and 614C can be looped through a portion of the device 612, similar to the single tether of previously described embodiments and attached to a location in the delivery system 600.

FIGS. 19-24 illustrate another embodiment of a delivery system that is generally similar to the previously described delivery system embodiments. A pusher 700 includes wires 706, 708 that are located within the inner diameter of the pusher 700. Typically, pushers are composed of a relatively thick core wire (such as core wire 412 in FIG. 6 to provide the rigidity needed to "push" the pusher within a catheter. However, as described in greater detail below, the pusher 700 lacks a traditional core wire, being instead composed of a plurality of hypotubes. This allows the pusher 700 to accommodate the wires 706, 708 within the hypotubes, instead of being located on the outside of the core wire).

Figure 22:
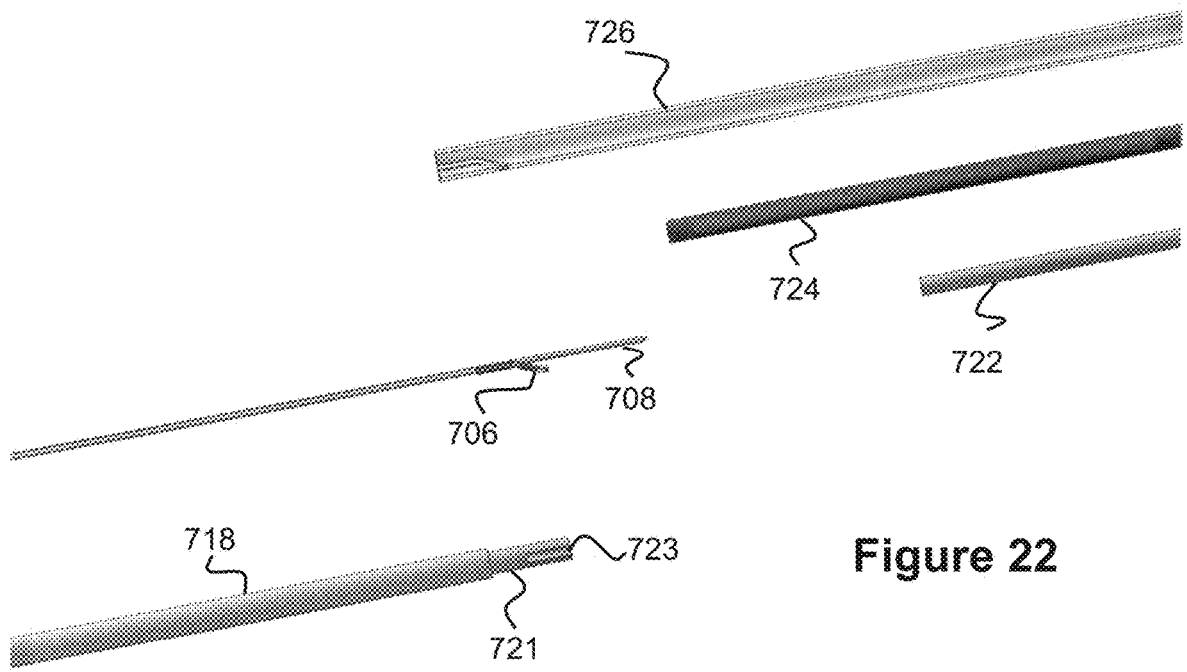
Figure 23:
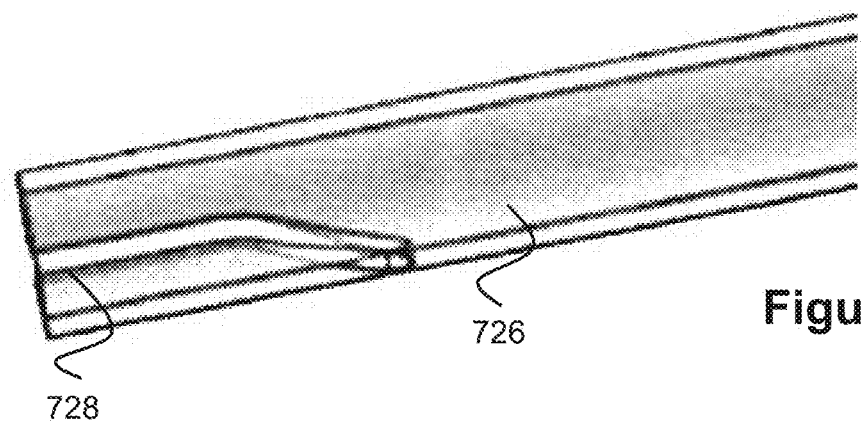

A distal portion of the pusher 700 can be seen best in FIGS. 19-21 as showing a coil assembly, while a proximal portion of the pusher 700 can been seen in FIGS. 22-24 as having a hypotube assembly connected to various other elements described in more detail below. Since pushers are generally pushed through a catheter to a target location, they require a substantial amount of rigidity and strength to prevent buckling or bending while being advanced through the tortuous pathway of a patient's vascular system. In this respect, pushers (such as those described in FIGS. 1-18 are mostly composed of a solid core wire along almost their entire length, with only a small tubular region disposed at the distal end of the pusher that houses a heater coil. In contrast, the embodiment below lacks a traditional core wire, being composed entirely by a tubular structure between its distal and proximal end, as discussed in detail below.

Figure 19:
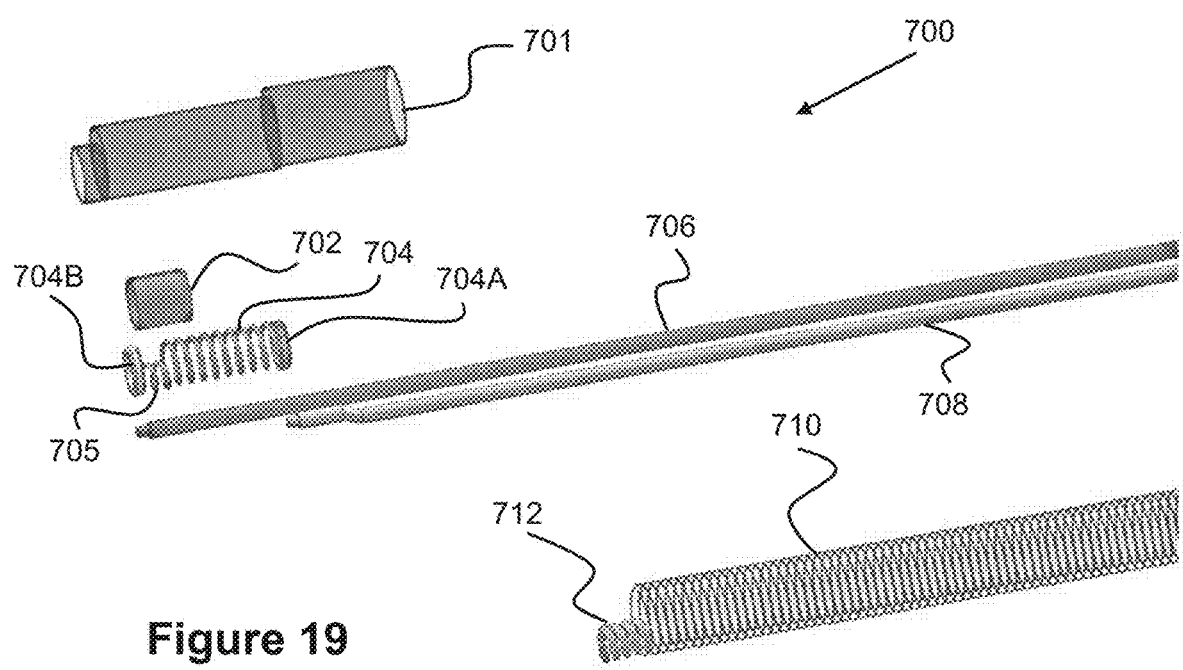
Figure 20:
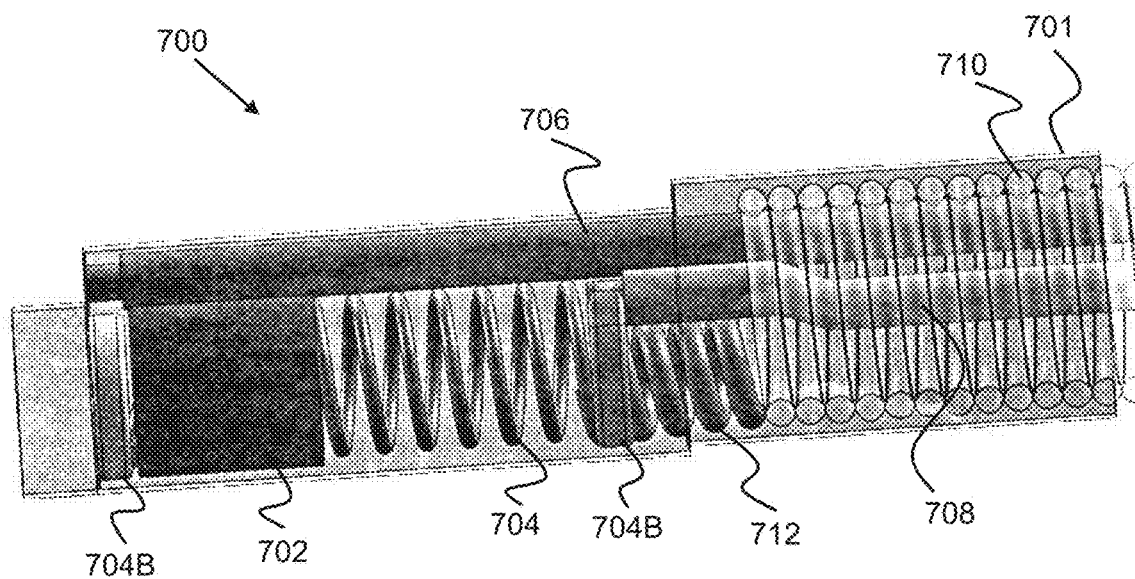

FIGS. 19-20 illustrate the distal-most portion of the pusher 700. Current is supplied to a heater 704 by lead wire 706, which connects (e.g., via solder) to a distal end 704B of the heater 704, and a lead wire 708 that connects to a proximal end 704B of heater 704. The wires 704, 706 are oppositely polarized to provide the current that flows through the heater to induce heat.

Any of the materials described in the other embodiments can be used for the heater 704. In one example the heater is a coil comprised of 92/8 platinum/tungsten alloy. The heater 704 may comprise a coil with 4-20 revolutions with a outer diameter of 0.005"-0.015" and a filar of 0.0005-0.002". In one example, the heater is a 12-revolution coil with a 0.0008" diameter filar and a 0.01" outer diameter. In another example, the heater is a 18-revolution coil with a 0.001" filar with an outer diameter of 0.01".

The heater may contain a smaller diameter region 705 located near or adjacent to the distal end 704B. A sleeve 702 is disposed over the smaller diameter region 705 of the heater to help insulate the patient from the heat generated by the smaller diameter region 705 and to ensure minimal heat dissipation so that more heat is available to sever the implant link. In one example the sleeve is comprised of polyimide. In one example, sleeve 702 contains a slit or channel which accommodates wire 706.

An over-sleeve 701 is disposed over the heater 704 and extends past the proximal end 704A of the heater 704 to help insulate or concentrate the heat of the heater and provide strain relief. The over-sleeve may be comprised of PET. In one example the over-sleeve is composed of black 1% carbon colorant impregnated PET. Carbon colorant impregnated PET offers increased lubricity compared to clear PTE and thus reduces friction with the inner catheter surface during delivery. The over-sleeve 701 helps bind all the elements within it together, adds another mechanical connection to bind the lead wires 706, 708, and helps prevent heat from dissipating to the patient. The over-sleeve 701 also helps hold the polyimide sleeve 702 that is placed over the heater's smaller diameter portion 712 to help focus the energy into the center of the heater element 704. The over-sleeve 701, in one example, may keep the heater coil 704 in a tensioned state to keep it from laterally compressing when a proximal pushing force is applied from via the proximal end of the pusher 700 by the user.

The heater 704 is proximally connected to a coil 710. In one example, coil 710 is a stainless steel coil with an outer diameter of 0.013" and a 0.0015" filar, pulled into a tension (i.e. greater than 0.025 ounces). The coil has a distal reduced diameter region 712 comprising a plurality of decreased diameter revolutions that facilitate the physical connection to the heater 704. The extra space around the reduced diameter region 712 allows room for the lead wires 706, 708 to connect to heater 704.

Figure 21:
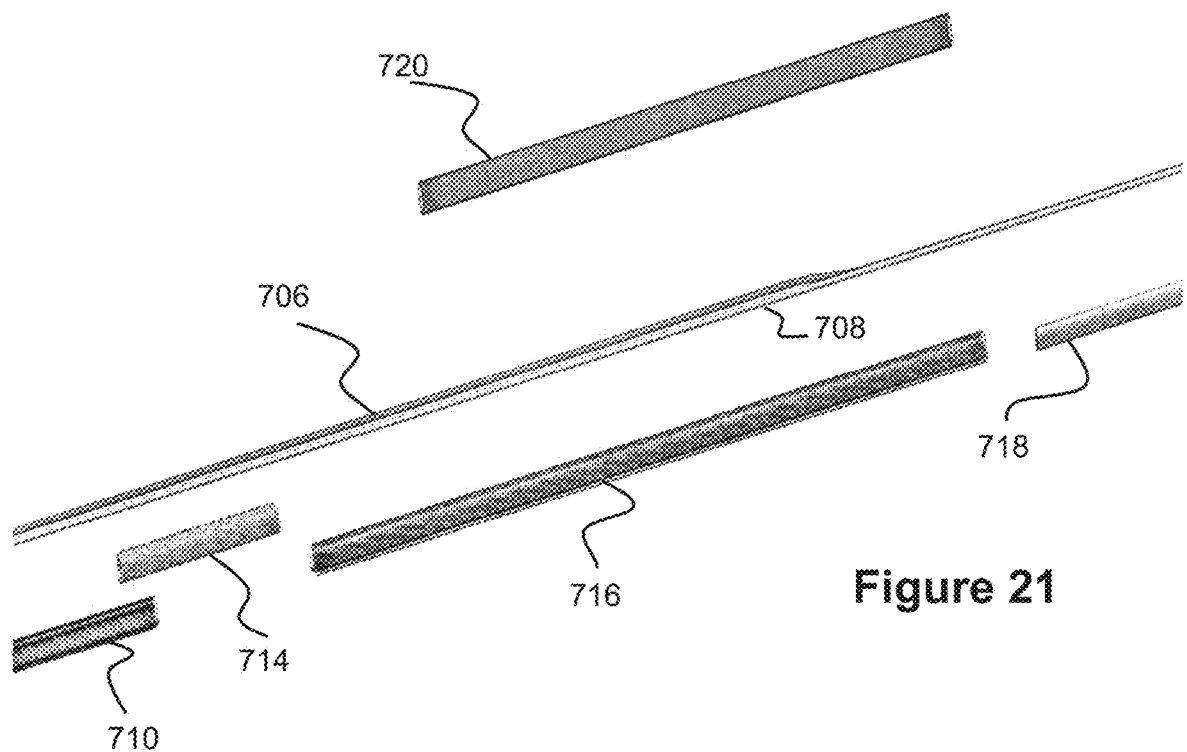
Figure 26A:
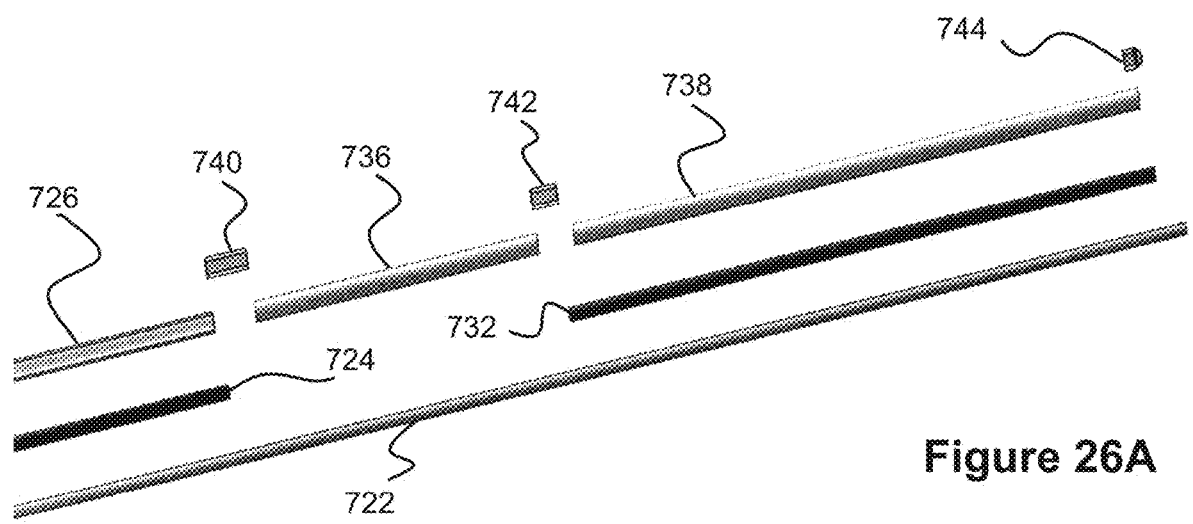
Figure 26B:
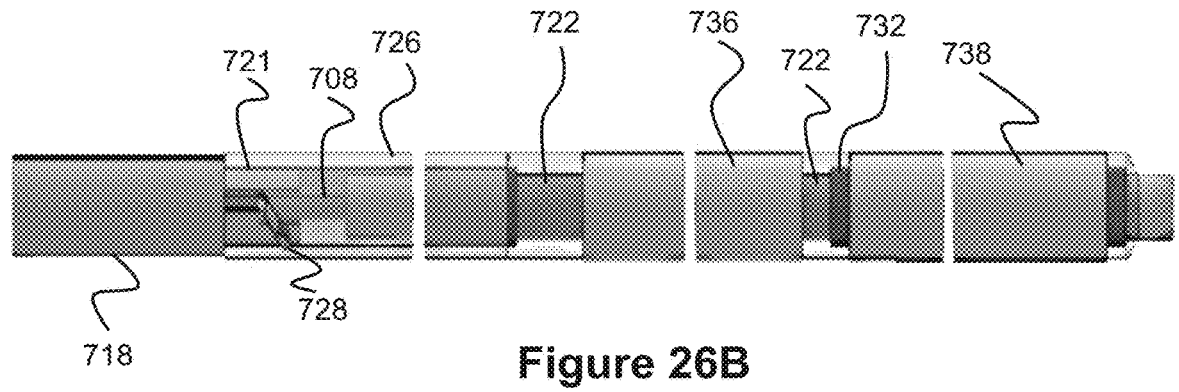
FIGS. 26B and 26C illustrate, respectively, a proximal portion of an implant delivery system and a complete view of an implant delivery system according to one embodiment.
Figure 26C:
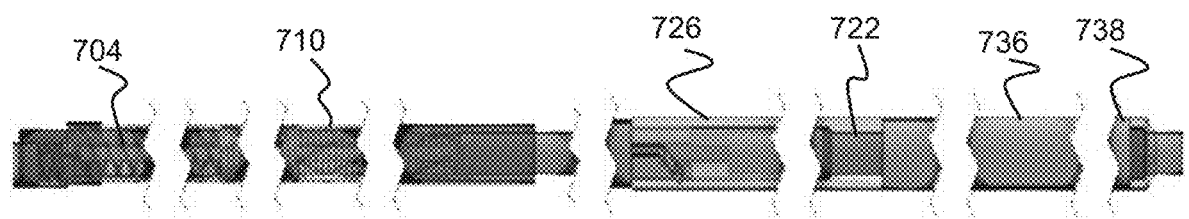
Figure 26D:
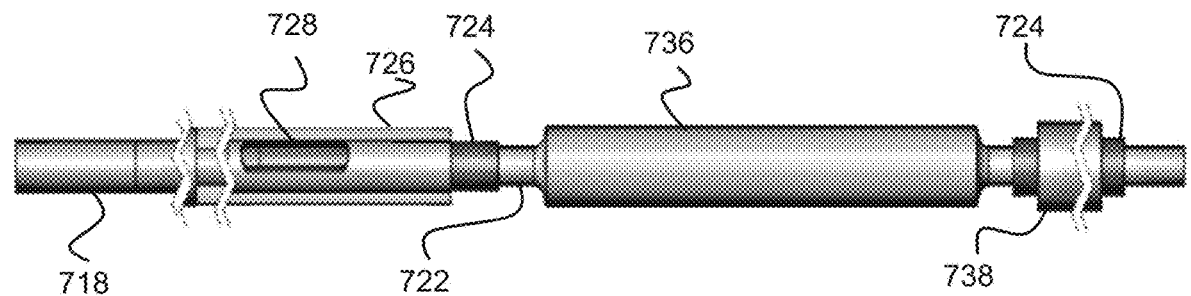
FIGS. 26D illustrates a proximal part of an implant delivery system according to another embodiment.
Figure 26E:
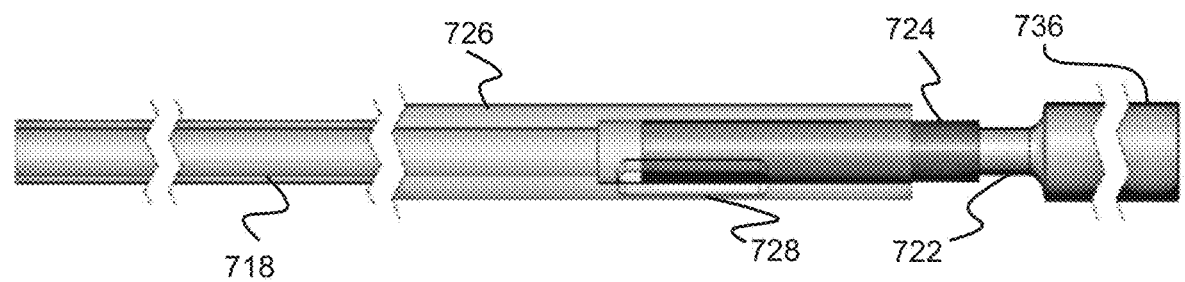
FIG. 26E illustrates a proximal part of an implant delivery system according to another embodiment.
Figure 26F:
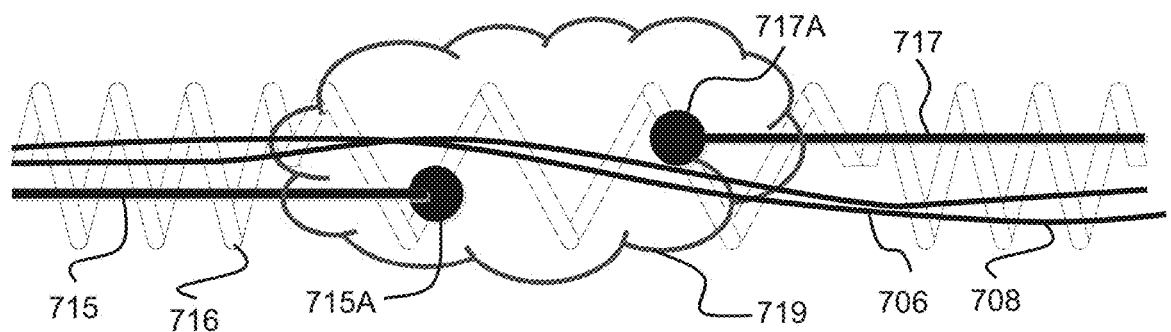
FIG. 26F illustrates a connection location on a structural coil for a stretch resistant wire and a tether.
Figure 26G:
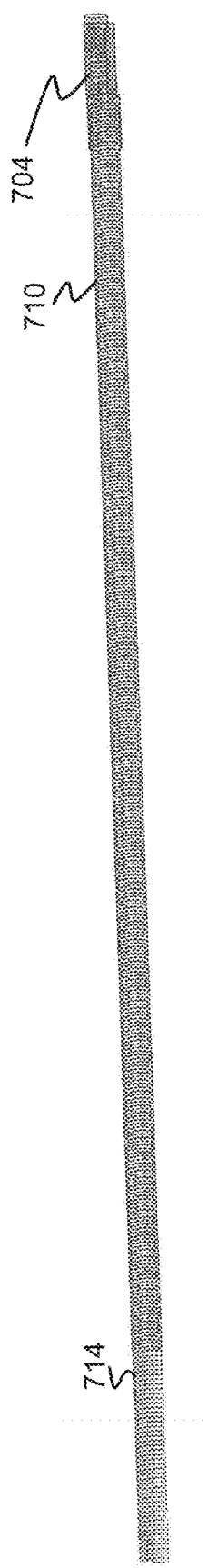
FIGS. 26G-26H illustrate the structural coils of one embodiment of an implant delivery system.
Figure 26H:
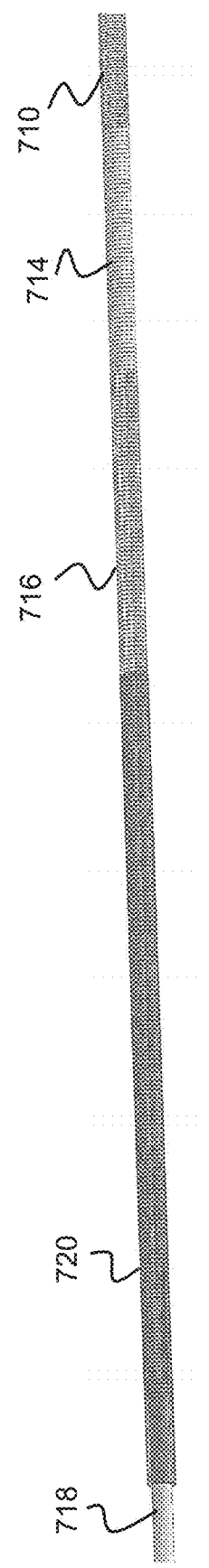

As best seen in FIGS. 21 and 26G-26H, the proximal end of coil 710 is connected to a marker coil 714. The marker coil 714 is preferably radiopaque and is roughly 3 centimeters from the distal tip of the pusher 700. In one example, marker coil 714 is comprised of a 92/8 platinum/tungsten coil with an outer diameter of 0.013" and a 0.002" filar. The marker coil 714 may be wound with an initial tension value (i.e. greater than 0.08 ounces). Another coil 716 is connected to the proximal end of the marker coil 714, which in one example is stainless steel with an outer diameter of 0.013" and a 0.002" filar, and is wound with an initial tension (i.e. greater than 0.1 ounces). Coil 716 is the longest piece of the coil portion of the assembly, in one example, reaching about 50-70 centimeters in length, and in another example being about 55 centimeters in length.

It is generally desirable to have a progressively lower stiffness from the proximal to the distal end of the pusher 700 in order to have high pushing strength from the proximal end and high flexibility at the distal end. This progressive stiffness can be achieved by winding the proximal coil 716 with a higher tension than the middle marker coil 714, which in turn is wound with a higher tension than distal coil 710, which in turn is wound with a higher initial tension than heater coil 704 as described in the example configuration of the preceding paragraph.

Tubing 720 is disposed over a portion of the coil 716 and optionally over a portion of hypotube 718 to help bind coil 716 and hypotube 718. The tubing may be comprised of black PET, in one example. Wires 706, 708, as described earlier, are located within the inner lumen of the coils.

The coil 716 of the pusher 700, shown in FIGS. 19-21 and 26F, may utilize a stretch resistant wire 717 (FIG. 26F) to prevent the coil 716 of the pusher 700 from unduly stretching during movement within a patient. In one example, this stretch resistant wire 717 is a 0.001" diameter stainless steel wire which can be welded at a proximal portion of the assembly (within coil 716) at weld area 717A, about 5 cm from the distal tip of the implant delivery system. This location at 5 cm from the distal tip is also within coil 716. The stretch resistant wire 717 may also be a polymer tether. In one example, the distal weld area 717A for the stretch resistant element is near the attachment location 715A for an implant attachment tether 715 which is connected to the implant (e.g., a microcoil) and which is severed (i.e. via heat) to release the implant. Preferably, adhesive 719 is disposed over both the weld area 717A and the tether attachment location 715A to further secure both attachment locations. In one example shown in FIG. 26F, coil 716 in the 5 cm from the distal tip zone is pulled into a more-open wound configuration compared to the rest of coil 716. In FIG. 26F, weld point location 715A of the implant tether 715 is shown as being distal to the weld point location 717A of the stretch resistant wire 717; however, this is not necessary. Rather, both weld locations 715A and 717A should be roughly within the same zone (i.e. about 5 cm from the distal tip). Thus weld area 715A could be proximal of distal of weld area 717A.

Coil 716 is connected proximally to hypotube 718. Hypotube 718 contains an inner lumen which accommodates wires 706, 708. The hypotube 718 may comprise most of the length of the pusher 700, which in one example is between about 80-150 cm, and in another example about 120 cm. The hypotube 718 may be made from a stainless steel tube with an outer diameter of 0.014" and an inner diameter of 0.007" so that the inner diameter is large enough to accommodate wires 706, 708.

Hypotube 718 may be tapered in one or more regions to increase pusher 700 flexibility. In one example, the taper begins near the distal end of the hypotube 718 and continues proximally for a certain length. In one example the taper begins at about 0.05" from its distal end where the outer diameter is about 0.0095" and continues proximally for about 30 centimeters where the outer diameter reaches about 0.014".

Hypotube 718, which contains both wires 706 and 708, may have a ground-down or thinned out proximal portion 721 (seen best in FIGS. 22, 24, and 25) to facilitate connection to the next section of the assembly, namely the tubular, outer polarized contact 726.

FIGS. 22-25 illustrate that the outer polarized contact 726 connects to lead wire 706, allowing an outside power supply to be connected to the pusher 700. Specifically, the contact 726 includes a distal slot 728, seen best in FIG. 25, that at least partially aligns with a proximal slot 723 in the thinned out proximal portion 721 of the hypotube 718. This arrangement of the slots 723 and 728 allow lead wire 706 to pass through the opening such that its uninsulated end contacts the contact 726, establishing electrical communication. In one example, wire 706 is soldered within slot 728 of contact 726. The polarized contact 726 is composed of a conductive material and in one example can be a gold plated hypotube.

Figure 24:
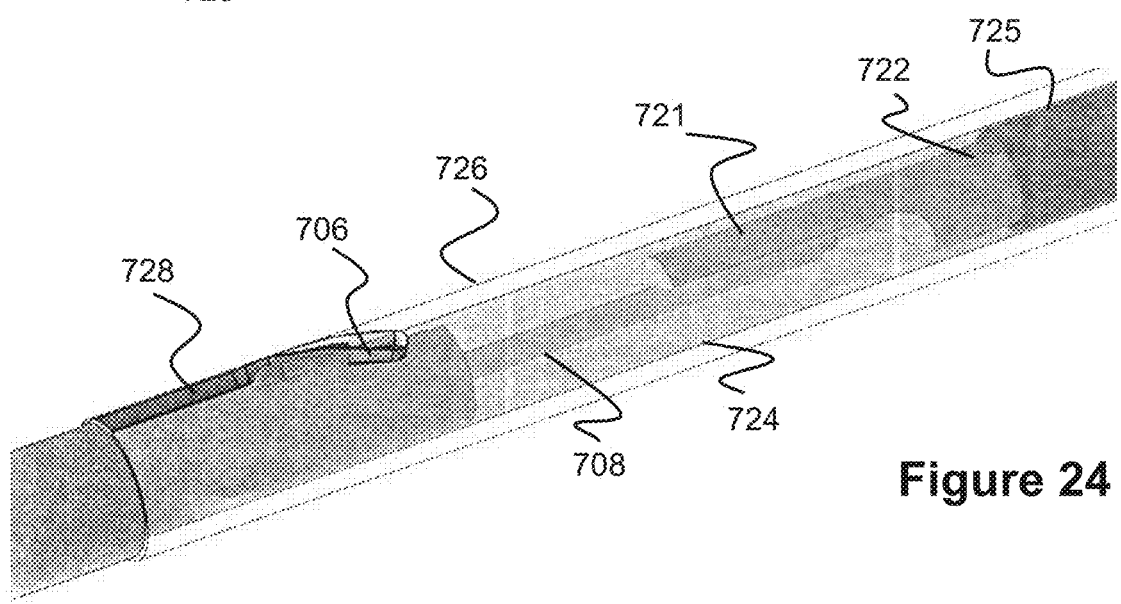
Figure 25:
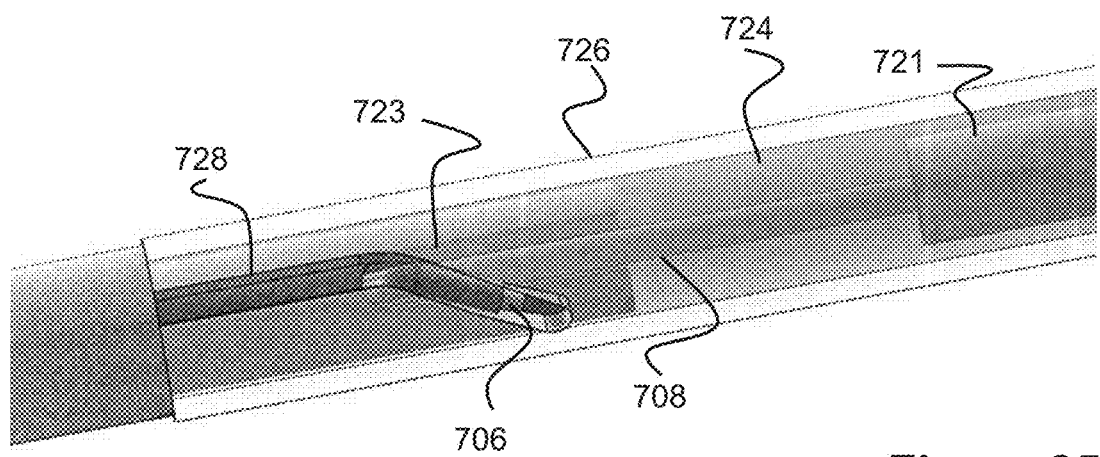

As best seen in FIG. 24, lead wire 708 extends further proximally to contact a recessed end 721 of a conductive inner mandrel 722. In one example, the uninsulated end of wire 708 is soldered to the recessed end 721 of inner mandrel 722, establishing electrical communication. Mandrel 722 and contact 726 are oppositely polarized to create a supply and return current flow path through the respective lead wires 706, 708. In one example inner mandrel 722 is gold plated and positioned within an insulating sleeve.

As with hypotube 718, the outer tubular contact 726 is disposed over the distal, recessed end 721 of the mandrel 722, but is also spaced apart by an insulator sleeve 724, which prevents electrical contact between the contact 726 and the mandrel 722. In one example, the insulator is a polyimide sleeve.

Mandrel 722 extends to the proximal end of the pusher 700, as shown in FIGS. 26A-C. The mandrel 722 is further covered by a proximal tubular electrical contact 736, located proximally adjacent to contact 726, and by a hypotube 738, located proximally adjacent to contact 736 (FIGS. 26A-26C). The contact 736 is in physical, electrical contact with the mandrel 722 but insulated from other components on the pusher 700, thereby forming the second electrical connection point for a power supply to connect to. More specifically, the contact 736 is electrically isolated from contact 726 and hypotube 738 by insulators 740 and 742 (e.g., epoxy or insulating tubes). Hypotube 738 is insulated from the mandrel 722 by insulating sleeve 732, while insulating sleeve 724 (e.g., polyimide) insulates the distal end of the mandrel 722 from the contact 726.

FIG. 26B shows the proximal end of the implant delivery system in which a user interface may be connected. In one example, the user interface is a handheld system, where the operator can press a button to initiate detachment of an implant (i.e. an embolic coil, stent, or other implant) by activating the heater at the distal end of the device. In one example a tether connects the pusher 700 to the implant, and this tether is severed when the heater 704 is activated and generates sufficient heat.

The user interface may have electrical contacts connected to conductive electrical contacts 726, 736, and 738. Wire 706 is connected to hypotube 726 as described earlier, and tubular contact 726 is one of the contacts connected to the user interface. Hypotube 726 has a first polarity. Contact 736 sits just proximal of contact 726. Wire 708 is welded inside inner mandrel/hypotube 722. Inner hypotube 722 is welded to hypotube 736. Since the inner hypotube is welded within hypotube 736 and both elements are conductive, the current is conveyed through hypotube 736, through inner hypotube 722, and through the wires. Contact 736 is another electrical contact point for the user interface and accepts a second polarity, opposed to the first polarity of contact 726. These current circuits provide a supply and return path for current which results in the heating of the heater, which acts as a resister between the two wires, thereby generating heat. The lead wires, as previously mentioned, traverse the inner diameter of the pusher.

Since proximal-most hypotube 738 is insulated from the rest of the circuit, it can be used by the power supply to sense if the pusher 700 is properly seated and, if not, prevent power from being delivered to the contacts 726 and 736. For example, the power supply may have four electrical contacts: one positioned to contact the contact 726, one positioned to contact the contact 736, and two positioned to contact the contact 738. When the pusher 700 is properly seated, the contact 738 completes a circuit between the two power supply contacts, and if the pusher 700 is even slightly unseated, at least one of the contacts loses physical contact with the contact 738, thereby interrupting the circuit. In this respect, the power supply can sense if the pusher 700 is properly seated. Additionally, the power supply can route the power for contacts 726 and 736 through the circuit created by contact 738, thereby preventing the power to contacts 726 and 736 from being turned on unless the pusher 700 is properly seated.

FIG. 26B shows the assembled view of FIG. 26A, while FIG. 26C shows the assembled view of the entire implant delivery system including the proximal end shown in FIGS. 26A and 26B.

FIGS. 26D-26E illustrate two other embodiments of the proximal end of the implant delivery system. The embodiment of FIG. 26D is similar to that of FIGS. 22-26C except this embodiment does not utilize a slot 728 at the distal end of tubular contact 726, but instead utilizes a slot 728 near the middle of contact 726, thus still coinciding with slot 723 of hypotube 718. Similar to the embodiments of FIGS. 22-26C, there are three contacts and hypotube/contact 726 accepts a first polarity, hypotube/contact 736 accepts a second, opposing polarity, and hypotube/contact 738 is used to turn the user interface on and off.

The embodiment of FIG. 26E is similar to the previous embodiments of FIGS. 22-26C, but instead utilizes only two contacts 726, 736, instead of three. Similar to the embodiment of FIG. 26, contact 726 utilizes a recess 728 at some point along the hypotube in order to allow a connection point for wire 706 and hypotube 726. A portion of hypotube 726 is electrically isolated via insulator 724 which sits under a portion of the hypotube. Another contact/hypotube 736 sits proximal of contact 726, and both contacts are electrically isolated from each other via insulator 724. Though this system utilizes two contacts, there may be three connection points with the user interface. One user interface contact may sit at a distal portion of hypotube 726 and be used to turn the unit on and off, and another interface contact sits at a more proximal point along hypotube 726 and has a first polarity. Another user interface contact sits on contact 736 and has a second polarity opposed to the first. The circuit is thus completed through the oppositely polarized wires 706, 708 where said wires are oppositely polarized due to the polarized contacts 726, 736.

Figure 27:
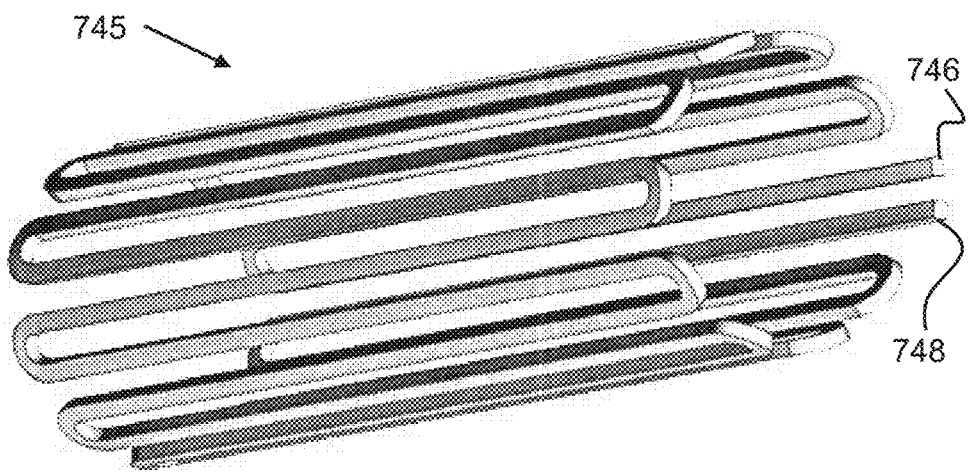
FIGS. 27-29 illustrate a hypotube heater utilized in an implant delivery system.

FIGS. 27-30 show various embodiments of a heater that can be used in any of the previously described implant delivery embodiments. Turning first to FIG. 27, a heater 745 is shown, having a generally tubular shape formed from a plurality of elongated regions that periodically have 180 degree curves. The heater 745 can be formed by cutting (e.g., laser cutting) a hypotube according to described pattern, which is also shown in a flattened state in FIG. 28. The heater 745 is preferably made from a high resistivity material to promote heat generation, such as platinum. It could be coated with an insulating material such as polyimide, polyethylene, Teflon, or paralyne. Alternately, the heater 745 can be formed from a sheet of material and curved into a tubular shape.

Figure 28:
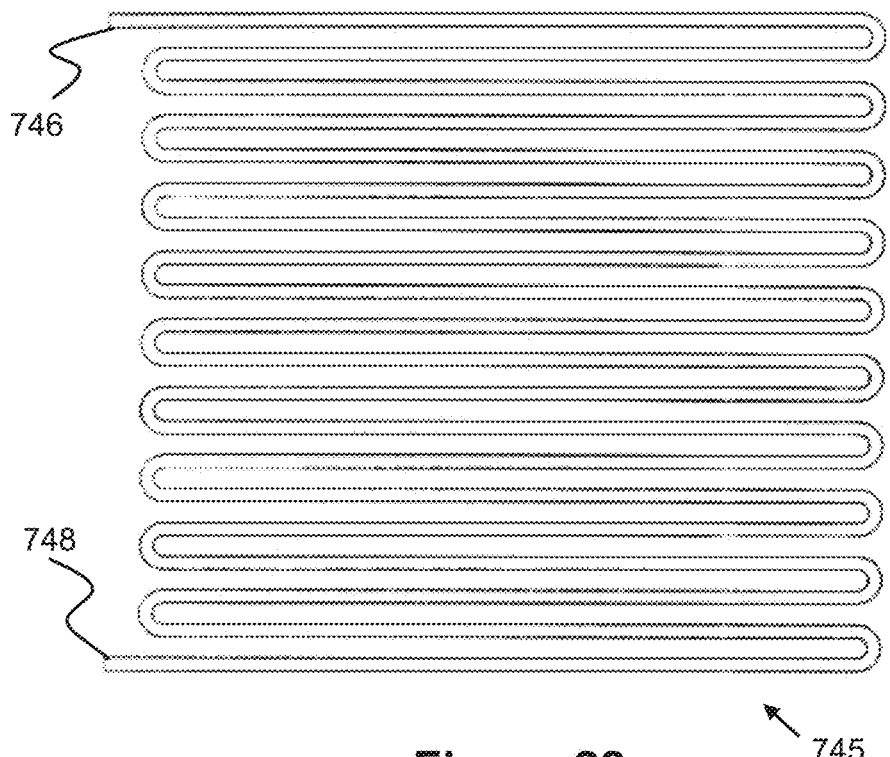
Figure 29:
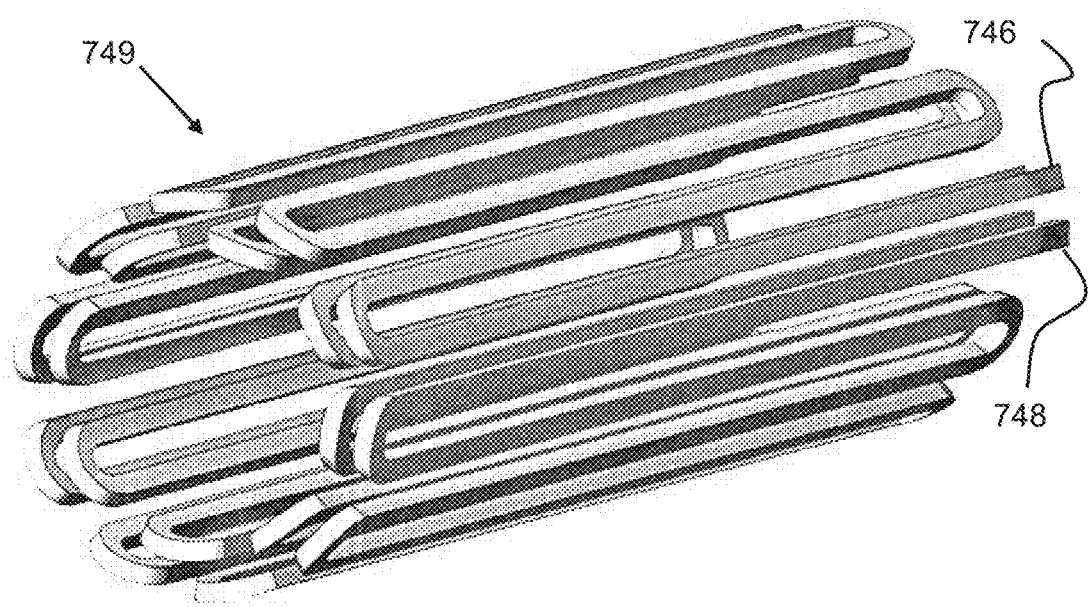

The pattern shown in FIG. 28 could be used as the one-layer configuration 745 shown in FIG. 27, or used as a multiple layer configuration 749 shown in FIGS. 29. The multiple layer configuration can be formed from two discreet tubular shapes in which a smaller diameter configuration is positioned within a larger diameter configuration. Alternately, an elongated sheet similar to the shape in FIG. 28 can be rolled into a helical, two layer configuration.

The lead wires connect to the hypotube at regions 746, 748 which are both located on the proximal end of the heater. Whereas the heater coils used in the previous implant delivery system embodiments require one coil connected to the proximal and another coil connected to the distal end of the coil, here both wires connect to the proximal end of the heater. One advantage of such a configuration is that there is no additional wiring that needs to be accommodated in the proximal to distal region of the heater, thus reducing the device profile within that region.

In one example, the heater is a laser cut flat-sheet that is rolled into a spiral pattern, has an inner diameter of 0.003" and an outer diameter of 0.012", and is rolled into two or more layers (i.e. an inner and outer layer, or an inner layer-middle layer-outer layer, or an inner layer-multiple middle layers-outer layer). This is offered just as a sample configuration, different variations are possible.

Figure 30:
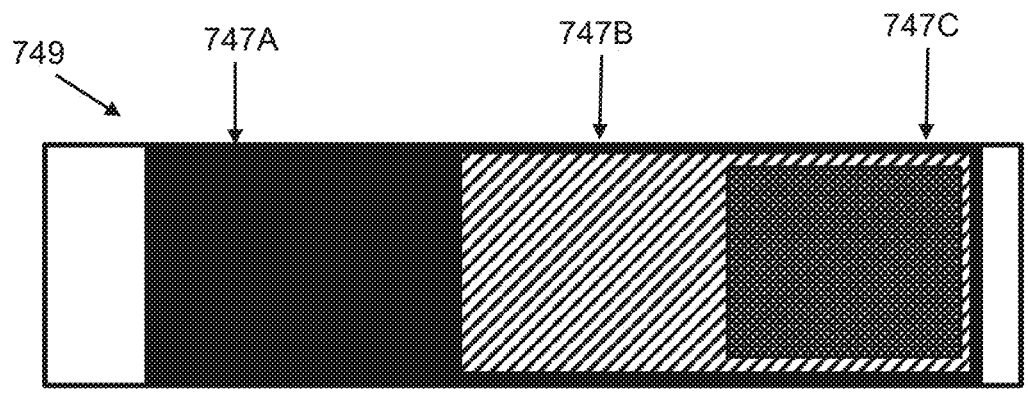
Figures 31A, 31B, 31C:
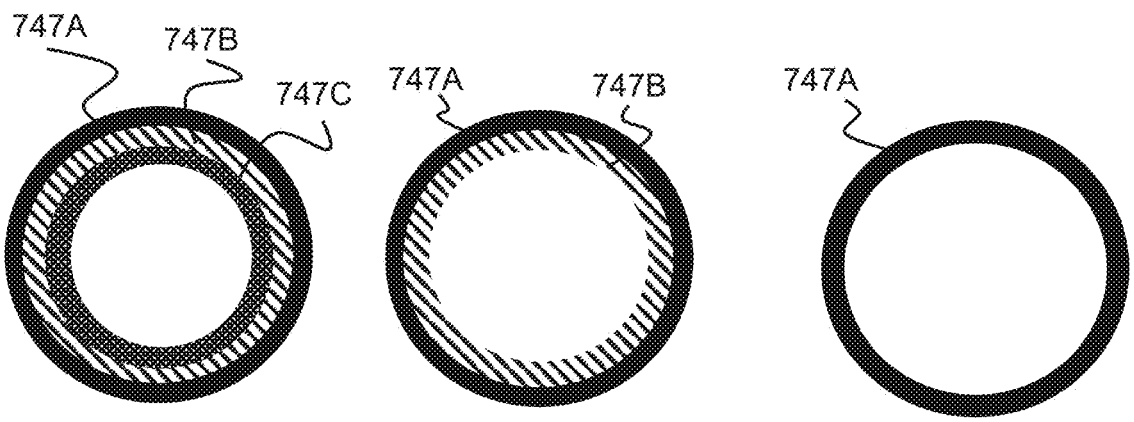

FIG. 30 illustrates another embodiment of a heater 749 having three staggered sections as shown in FIG. 30. In one example, layer 747a spans the entire section of the heater 749, layer 747b spans less than the entire section of the hypotube, and layer 747c spans only a proximal section of the heater 749. This staggered configuration allows variable heating in different sections of the heater. While three staggered sections are shown, other numbers of staggered layers are possible, such as two, four, five, and six or more.

This staggered configuration can be created by staggering several flat, cut sheets on top of each other at the desired positions, then rolling the layers to create the multiple layer heater 749. In another example, each staggered section is its own rolled hypotube, and subsequent sections are placed within in each other to create the staggered profile. In one example, the specific detachment point would be located at one of the staggered areas, where the staggered portions overlap with each other, since the generated heat is maximized at the staggered areas.

In addition to the rolled multiple layer designs 749 of FIG. 30, discrete layers could be placed within in each other to produce such a configuration. Each layer could have separate positive and negative terminals and associated wiring, or the heater could be connected to a common circuit which selectively heats one or more of the layers. This discrete, multiple layer configuration could also be used with the staggered profile concept shown in FIG. 30.

FIGS. 30a-30c show a cross section of a staggered profile hypotube from a proximal (FIG. 30a), medial (FIG. 30b), and distal (FIG. 30c) section of the hypotube. In this example, the layers are staggered such that the proximal region contains three layers, medial region contains two layers, and the distal region contains only one layer. The staggered cross-sectional profile corresponds to the staggered profile shown in FIG. 30.

Figure 32:
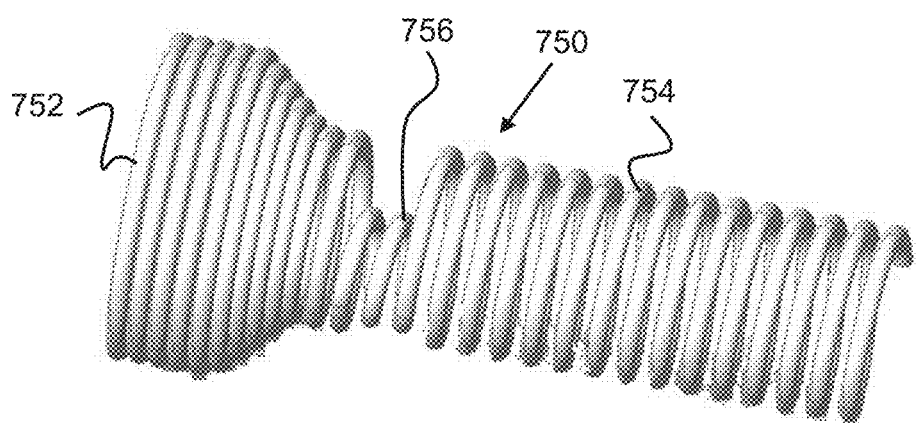
FIGS. 32-33 illustrate an implant delivery system with an enlarged distal section.
Figure 33:
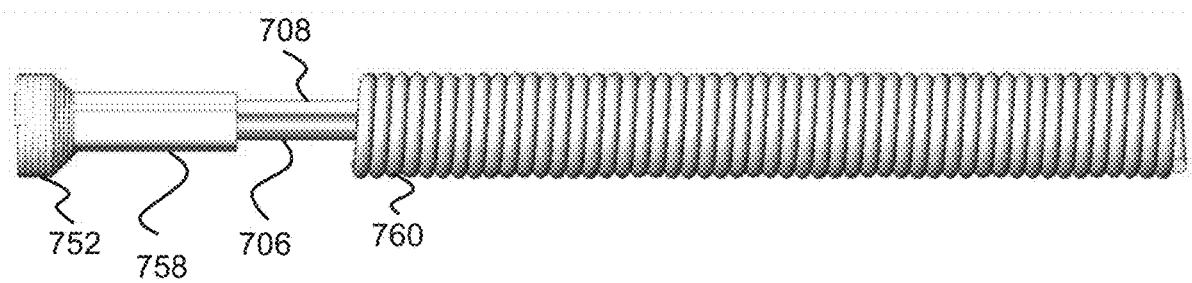

FIGS. 32-33 show an alternative embodiment of a heater coil 750 for a pusher. The heater 750 is similar to the heater 704 of FIG. 19, comprising a first region 754 having a first diameter, and second region 756 having a second diameter smaller than the first. A larger diameter region 752 is located distal to the smaller diameter region 756. The actual heating component may run from the proximal end of the portion 754 to the second region 756, or from the proximal end of portion 754 to a proximal part of larger diameter region 752, or solely from the proximal to distal end of section 754, depending on where the first and second wires are connected.

In the embodiment of FIG. 19, the polymer over-sleeve 701 could potentially contact the inner surface of the catheter that the pusher 700 is advanced through. In the embodiment 750 shown in FIGS. 32-33, the metallic, larger diameter region 752 contacts the inner surface of the catheter, making tracking easier due to the decreased contact area, as well as the typically lower frictional properties of metals compared to polymers. Alternately, region 752 can be sized so as to not contact the inner surface of the catheter.

Another advantage also relates to ease of pushing. In the embodiment of FIG. 19, though the polymeric over-sleeve 762 can be placed over the coil while the coil is in tension, the coil may still compress slightly when a proximal pushing force is applied via the pusher depending on the amount of force applied. This compression absorbs some of the pushing force exerted from the proximal end of the device. In addition, since the pusher is positioned directly over the heater, less heat dissipates. Also, since the pusher directly contacts the enlarged section and the wires sit underneath the pusher, the electric lead wires receive little stress from the pusher.

Referring to FIG. 33, the distal end of the structural coil 760 of the pusher directly contacts or abuts the distal, enlarged diameter section 752 of the heater. The enlarged diameter region 752 of the heater is close wound, preferably with a minimal gap or no-gap configuration, thus the proximal pushing force will not affect the shape of said enlarged diameter region 752, resulting in easier trackability. Since the distal end of the structural coil 760 connects at the distal portion of the heater 750 instead of the proximal end, it reduces the likelihood of the heater 750 bending or kinking during a procedure, especially if a smaller and therefore weaker segment, such as section 756 is present.

A polymeric over-sleeve 758 may still be placed over a proximal section of the heater 750 as shown in FIG. 33 in order to provide insulation and prevent the generated heat from dissipating. Sleeve 758 can be polyimide, polyethylene, Teflon, or paralyne. As shown in FIG. 33, the outer tubular member 762 directly abuts region 752 and sits over heater sections 754, 756. Lead wires 706, 708—similar to the embodiments of FIG. 19, sit within the inner diameter of the pusher.

Figure 34:
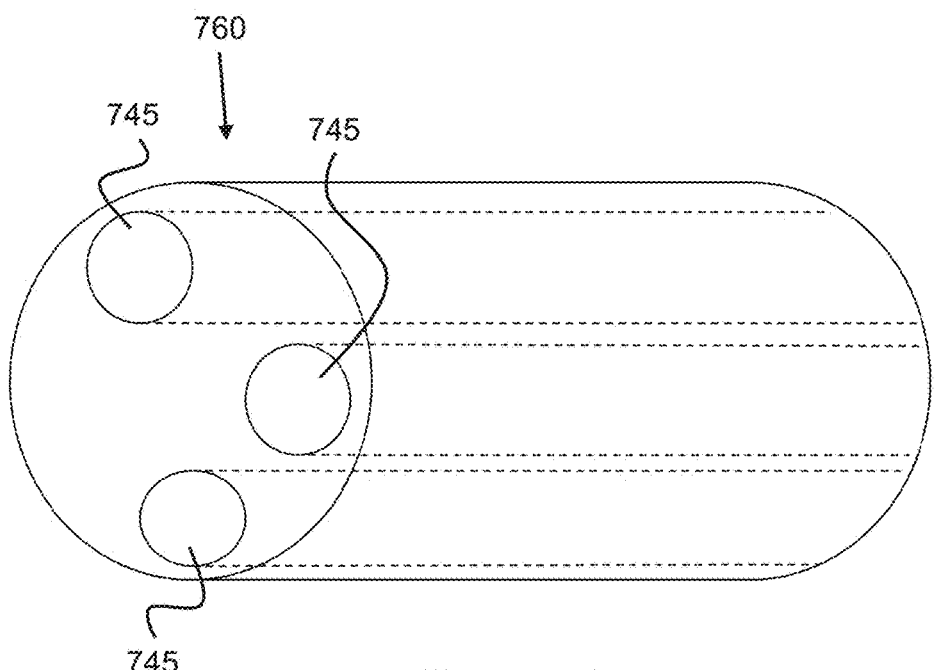
FIG. 34 illustrates a heater utilizing multiple hypotube heating elements.

FIG. 34 illustrates another embodiment of a pusher 760 containing multiple (i.e. 2 or more) hypotube heaters, like the ones shown in FIGS. 27-29. Like the hypotubes of FIGS. 27-29, the positive and negative wire terminals are both at the proximal end of the heater. Epoxy could be used around each hypotube heater to insulate the heat and prevent electrical discharge between the various hypotubes. In one example, the cylinder could be comprised of a polymer in order to minimize heat loss and conductivity between the hypotube heaters and the cylinder housing said hypotube heaters.

In another embodiment the heater is created via 3d printing techniques.

Although the invention has been described in terms of particular embodiments and applications, one of ordinary skill in the art, in light of this teaching, can generate additional embodiments and modifications without departing from the spirit of or exceeding the scope of the claimed invention. For example, the heater coil or heater coil expander could be constructed to activate a switch that provides a user indication of detachment in some manner. Additionally, a visual indicator may be associated with the change in resistance to provide easy indication of detachment. Accordingly, it is to be understood that the drawings and descriptions herein are proffered by way of example to facilitate comprehension of the invention and should not be construed to limit the scope thereof.

What is claimed is:

1. A pusher for delivering a medical implant, comprising:
    an elongated pusher body having a proximal end and a distal end;
    a heater located at said distal end of said elongated pusher and being configured to cause detachment of an implant when activated; and, a first sleeve disposed over said heater; said first sleeve being composed of carbon colorant impregnated polymer material.

2. The pusher of claim 1, wherein said first sleeve is composed of black 1% carbon colorant.

3. The pusher of claim 1, wherein said polymer material is polyethylene terephthalate (PET).

4. The pusher of claim 1, wherein said first sleeve is configured to reduce friction on an outer surface of said pusher.

5. The pusher of claim 1, wherein said heater is a resistance heater coil.

6. The pusher of claim 1, wherein said heater is a resistance heater coil having a first region forming a first internal diameter, and a second region forming a second internal diameter; and wherein a second sleeve is disposed over said second region and underneath said first sleeve.

7. The pusher of claim 1, wherein said heater is a resistance heater coil and wherein said first sleeve is disposed over said heater coil so as to maintain a radial tension of said heater coil.

8. The pusher of claim 1, wherein said proximal end of said elongated pusher body further comprises a first electrical contact, a second electrical contact, and a third electrical contact.

9. A pusher for delivering a medical implant, comprising:
an elongated pusher body having a proximal end and a distal end;
a heater located at said distal end of said elongated pusher and being configured to receive electrical current from said proximal end of said elongated pusher body; and,
a first sleeve disposed over said heater; said first sleeve being composed of a polymer material and a carbon colorant.

10. The pusher of claim 9, wherein said first sleeve is impregnated with said carbon colorant.

11. The pusher of claim 9, wherein said carbon colorant is black 1% carbon colorant.

12. The pusher of claim 9, wherein said heater has a first region forming a first internal diameter, and a second region forming a second internal diameter; and wherein a second sleeve is disposed over said second region and underneath said first sleeve.

13. The pusher of claim 12, wherein said heater has a first region forming a first internal diameter, and a second region forming a second internal diameter; and wherein said first sleeve is disposed over said first region and said second region.

14. The pusher of claim 9, wherein said first sleeve is disposed over said heater so as to maintain a radial tension of said heater.

15. The pusher of claim 9, wherein said proximal end of said elongated pusher body further comprises a first electrical contact, a second electrical contact, and a third electrical contact.

16. The pusher of claim 9, wherein said polymer material is polyethylene terephthalate (PET).

17. The pusher of claim 9, wherein said heater is a heater coil.

* * * * *